US011745038B2

(12) United States Patent
Gish

(10) Patent No.: US 11,745,038 B2
(45) Date of Patent: Sep. 5, 2023

(54) APPARATUS AND SYSTEM FOR DECENTRALIZED ELECTRICITY GENERATION AND POWER CONDITIONING

(71) Applicant: Peter A. Gish, Hanover, NH (US)

(72) Inventor: Peter A. Gish, Hanover, NH (US)

( * ) Notice: Subject to any disclaimer, the term of this patent is extended or adjusted under 35 U.S.C. 154(b) by 90 days.

(21) Appl. No.: 17/534,793

(22) Filed: Nov. 24, 2021

(65) Prior Publication Data

US 2022/0080246 A1 Mar. 17, 2022

Related U.S. Application Data

(63) Continuation of application No. 16/848,547, filed on Apr. 14, 2020, now Pat. No. 11,213,711, which is a continuation of application No. 16/056,103, filed on Aug. 6, 2018, now Pat. No. 10,661,111.

(51) Int. Cl.
| | | |
|---|---|---|
| *A63B 21/005* | (2006.01) | |
| *G06F 3/048* | (2013.01) | |
| *G05F 1/66* | (2006.01) | |
| *G06F 1/16* | (2006.01) | |
| *G05B 13/02* | (2006.01) | |
| *G16Z 99/00* | (2019.01) | |

(52) U.S. Cl.
CPC ...... *A63B 21/0055* (2015.10); *A63B 21/0058* (2013.01); *G05F 1/66* (2013.01); *G06F 3/048* (2013.01); *G05B 13/02* (2013.01); *G06F 1/1692* (2013.01); *G16Z 99/00* (2019.02)

(58) Field of Classification Search
CPC ............ A63B 21/0055; A63B 21/0058; G05B 13/02; G05F 1/66; G06F 1/1692; G06F 3/048; G06F 19/00
See application file for complete search history.

(56) References Cited

U.S. PATENT DOCUMENTS

| | | | |
|---|---|---|---|
| 3,240,947 A | 3/1966 | Mas | |
| 8,888,660 B1 | 11/2014 | Oteman | |
| 9,873,014 B1 | 1/2018 | Kuo | |
| 9,901,767 B2 | 2/2018 | Kuo | |
| 11,040,231 B2 * | 6/2021 | Rubin | ................ A63B 71/0622 |
| 2008/0172328 A1 | 7/2008 | Ajilian | |
| 2009/0054207 A1 | 2/2009 | Lin | |
| 2009/0251296 A1 | 10/2009 | Whelan | |
| 2009/0271336 A1 | 10/2009 | Franks | |
| 2010/0036736 A1 | 2/2010 | McGee | |

(Continued)

*Primary Examiner* — Joshua Lee
(74) *Attorney, Agent, or Firm* — Hunton Andrews Kurth LLP

(57) ABSTRACT

An electric generator which can be coupled to an exercise machine is described. The electric generator is connected to a power grid. Using the mechanical movements of the exercise machine, the generator can produce and feed electricity into the grid, thereby creating a decentralized grid system which is immune to node failures. The generator can communicate with a smart device of a user. The generator can inform the user of the amount of electricity generated by the user while working out. The generator or an application of the smart device can communicate this data to a service provider. Using this data, the service provider can pay the user for the electricity generated. In particular, the service provider can utilize a cryptocurrency to reward the user for the human generated electricity.

19 Claims, 13 Drawing Sheets

(56) References Cited

U.S. PATENT DOCUMENTS

| | | |
|---|---|---|
| 2010/0197460 A1 | 8/2010 | Czarnecki |
| 2010/0197461 A1 | 8/2010 | Czarnecki |
| 2011/0009239 A1 | 1/2011 | Whelan |
| 2011/0263384 A1 | 10/2011 | Drazan |
| 2011/0307314 A1 | 12/2011 | Frumer |
| 2012/0253489 A1 | 10/2012 | Dugan |
| 2014/0018966 A1 | 1/2014 | Yao |
| 2014/0066257 A1 | 3/2014 | Shavit |
| 2014/0296033 A1 | 10/2014 | Frumer |
| 2017/0070050 A1 | 3/2017 | Wang |
| 2018/0006526 A1 | 1/2018 | Sundria |
| 2018/0214729 A1* | 8/2018 | Rubin ............ A63B 24/0087 |
| 2018/0264314 A1 | 9/2018 | Kuo |
| 2019/0030398 A1 | 1/2019 | Kuo |
| 2019/0299079 A1 | 10/2019 | Trahan |
| 2019/0344123 A1* | 11/2019 | Rubin ............ A63B 24/0062 |

* cited by examiner

APPARATUS AND SYSTEM FOR DECENTRALIZED ELECTRICITY GENERATION AND POWER CONDITIONING

BACKGROUND

Electric power for a geographical region or country is provided through an electric power distribution network or grid. An electric power distribution network can have several power plants. Each one of the power plants can have numerous power generators. The power generators can be fossil fuel generators, solar generators, wind generators, etc. Each one of these power plants can be a node in the electric power distribution network. In larger networks, while the designers strive to build a failure-proof network, occasionally node failures occur due to poor power quality. As a result, if the power distribution network is not prepared for a failure event, there can be power outages throughout the network causing severe disruption to business and residences.

SUMMARY

There are several approaches for addressing potential power network failure issues. One approach is to minimize the network's dependence on any single node or power plant in the network, i.e., to diversify the sources of electric power production. In a diversified network, if a node failure occurs, the network is less likely to fail because the network is not very dependent on any single node. An example of a diversified network can be a network in which houses have solar panels and feed power back into the network.

Recent developments in electric power generation technology have made it possible to add smaller scale power generation systems to an electric power distribution network. For example, certain residential houses include solar panels which can generate electrical energy from sunlight. These household systems can supply electric energy for household needs, and in case the generated electricity exceeds the immediate need of the household, the energy can be stored in a power storage unit, such as a battery, or can be optimized ("conditioned") and then supplied to the electric grid. Some electric companies purchase the excess generated power and pay the homeowners for the excess energy produced. There are several benefits to supplying electricity from residences to an electrical grid. First, to the extent the task of providing electric energy to the grid can be divided between more nodes (here between houses and power plants), the system is more diversified. Hence, failure of one power plant would not necessarily lead to the failure of the entire network. In addition, diversified power networks provide better power quality. Therefore, there are benefits to establishing new distributed power generation systems which can connect to an electric power distribution network so that the network's dependence on any single power plant or node is reduced or eliminated.

An objective of this disclosure is to provide for a device, software application program and system which can facilitate network diversification by feeding high power quality human generated electricity into the grid. In an example embodiment, an electric generator is coupled to an exercise machine in a gym. The electric generator is connected to a power grid. Using the mechanical energy generated through use of the exercise machine, the generator can produce and feed electricity into the grid, thereby creating a decentralized grid system which is immune to node failures. The generator can communicate with a smart device such as a phone or tablet of a user. The generator can thereby inform the user of the amount of electricity generated by the user while the user is working out. The generator or an application of the smart device can communicate this data to a service provider. Using this data, the service provider can remunerate the user for the electricity generated. In particular, the service provider can utilize a cyber-currency to compensate the user for the human generated electricity.

There are several benefits to utilizing the device, software application program and system as described herein. If they are implemented in all exercise machine suitable for power generation in a typical commercial gym in a large city, the electricity consumption of the gym could be cut almost in half, and upwards of 25 kWh of conditioned high quality electricity could be injected into the grid each day, thereby reducing the risk of node failures. In addition, if the proper legal framework is implemented, human generated electricity could qualify for certified emission reduction (or "carbon") credits as well as federal, state and local production tax credits.

Human generated electricity can result in health benefits for society. These health benefits can include improved cardio-vascular fitness, better muscle-tone, weight loss, greater mental acuity, stress reduction, and a feeling of wellness and purpose. Utilizing the device, software application program and system as described herein, each participating user can monitor the user's progress in real time. As a consequence, the user sees in real time quantifiable and accumulated benefits from each workout. Additionally, because the user is compensated by means of the cyber-currency for the user's workout, the user is encouraged to workout even more, thereby further reducing the risk of node failures in the electric grid.

Human generated electricity can also bring about social benefits for the participants. These benefits can be direct benefits and web-derived benefits. The direct social benefits include participating in organized classes at a local fitness center (e.g., spinning classes) and the attendant social interactions that ensue. Web-based social benefits include interacting with other users through social media platforms, cross-pollination with other social media platforms, and targeted advertising.

Compensating human generated electricity using a cyber-currency can also be extremely advantageous for promoting a resilient electricity grid less prone to failures. The cyber-currency platform can become a trading tool for companies and entities interested in promoting human generated electricity, e.g., for tax purposes, health benefits or social benefits. By being able to transact the cyber-currency using an independent financial instrument, these companies can indirectly purchase human generated electricity without having to get involved in the process of generating the electricity. At the same time, the cyber-currency can also quantify the extent of involvement of each company in this effort.

DETAILED DESCRIPTION

Exercise Machine

Figure 1:
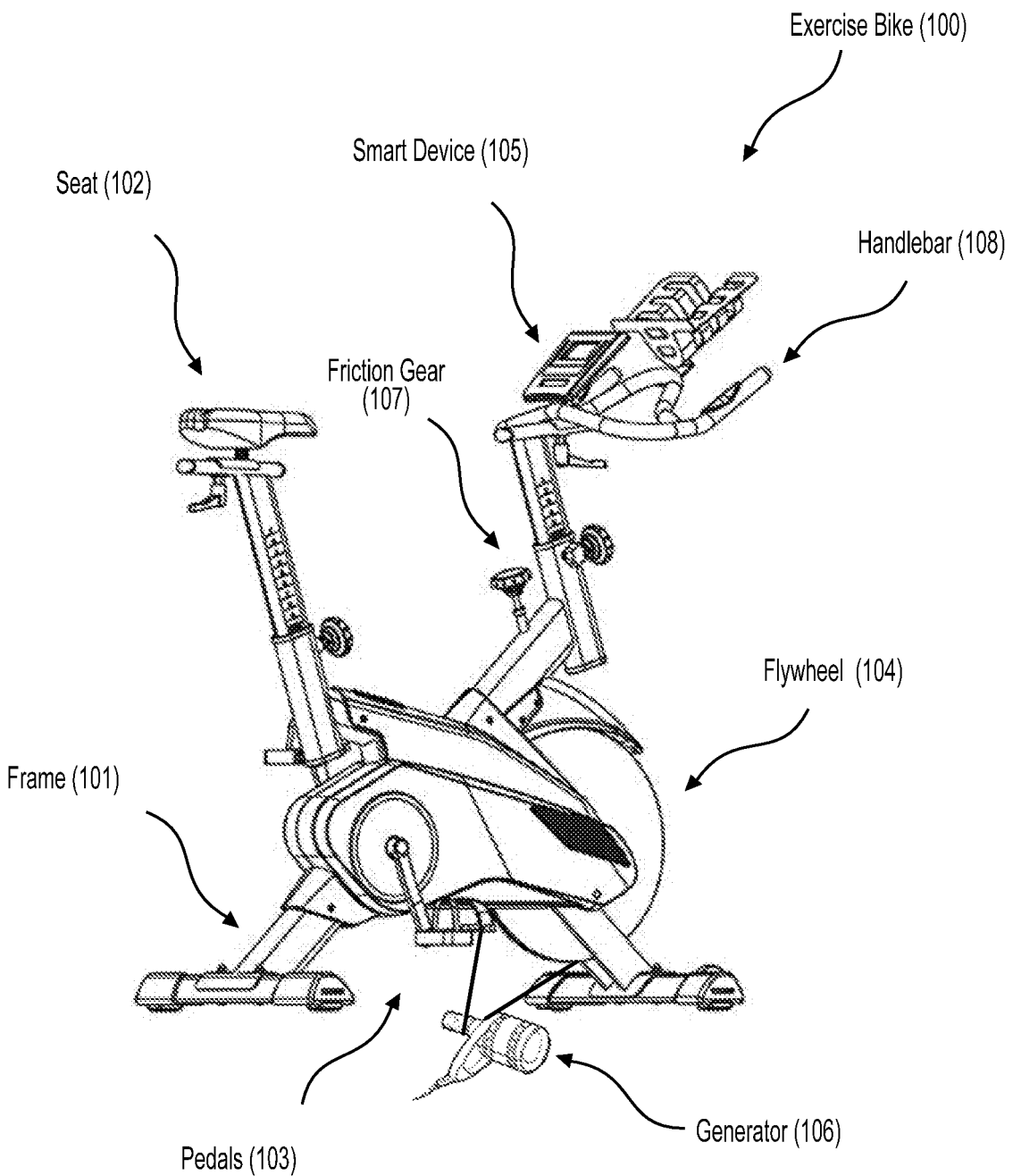
FIG. 1 shows an exercise bike according to an example embodiment.

In an example embodiment, the exercise machine can be an exercise bike. FIG. 1 shows an exercise bike 100 according to an example embodiment. The exercise bike 100 can include a frame 101, a seat 102, a set of pedals 103, a flywheel 104, a smart device 105 and a handlebar 108. The set of pedals 103 can be connected to the flywheel 104 via a chain or other connection mechanism.

In some embodiments, the exercise bike 100 can include an electricity generator 106 (or generator). The generator 106 can be mechanically coupled or connected to flywheel 104. When a user of the exercise bike 100 pedals the bike, the flywheel 104 rotates and this rotation can be mechanically transferred to the generator 106. For example, the generator 106 can be mechanically connected to the flywheel 104 using a chain or belt. As another example, the generator can be placed under the flywheel 104 so that a rotational component of the generator 106 is in contact with the flywheel 104.

The smart device 105 can be paired with the generator 106 and can be placed on the handlebar 108. The smart device 105 can be a smartphone, a cell phone, a laptop, a desktop, a notebook, a tablet, a wearable device, etc. In one embodiment, the smart device 105 can be fixed to the exercise machine, e.g., exercise bike 100. In another embodiment, the smart device 105 can be attachable to and detachable from the exercise machine. Yet in another embodiment, the smart device 105 is a separate device which does not attach to the exercise machine.

The smart device can include an application which can display a user interface through which a user can increase or decrease the load or resistance of the generator 106. Once paired, the smart device can transmit a command to the generator 106 to increase or decrease the load or resistance of the generator 106. Because the generator 106 is in contact with or coupled to the flywheel 104, an increase in the load or resistance of the generator 106 can increase the load or resistance of the flywheel 104. As a result, by increasing the load of the generator 106, the user can feel a heavier load when pedaling.

In some embodiments, the exercise bike 100 can include a friction gear 107. The friction gear 107 can produce frictional damping of the flywheel. When the friction gear 107 is applied, the user can feel a load or resistance when pedaling. In one embodiment, the friction gear 107 can be an electrical friction gear. In this embodiment, the frictional gear 107 can be paired with the smart device 105, and using the smart device 105, the user can increase or decrease the frictional damping of the flywheel.

Figure 2:
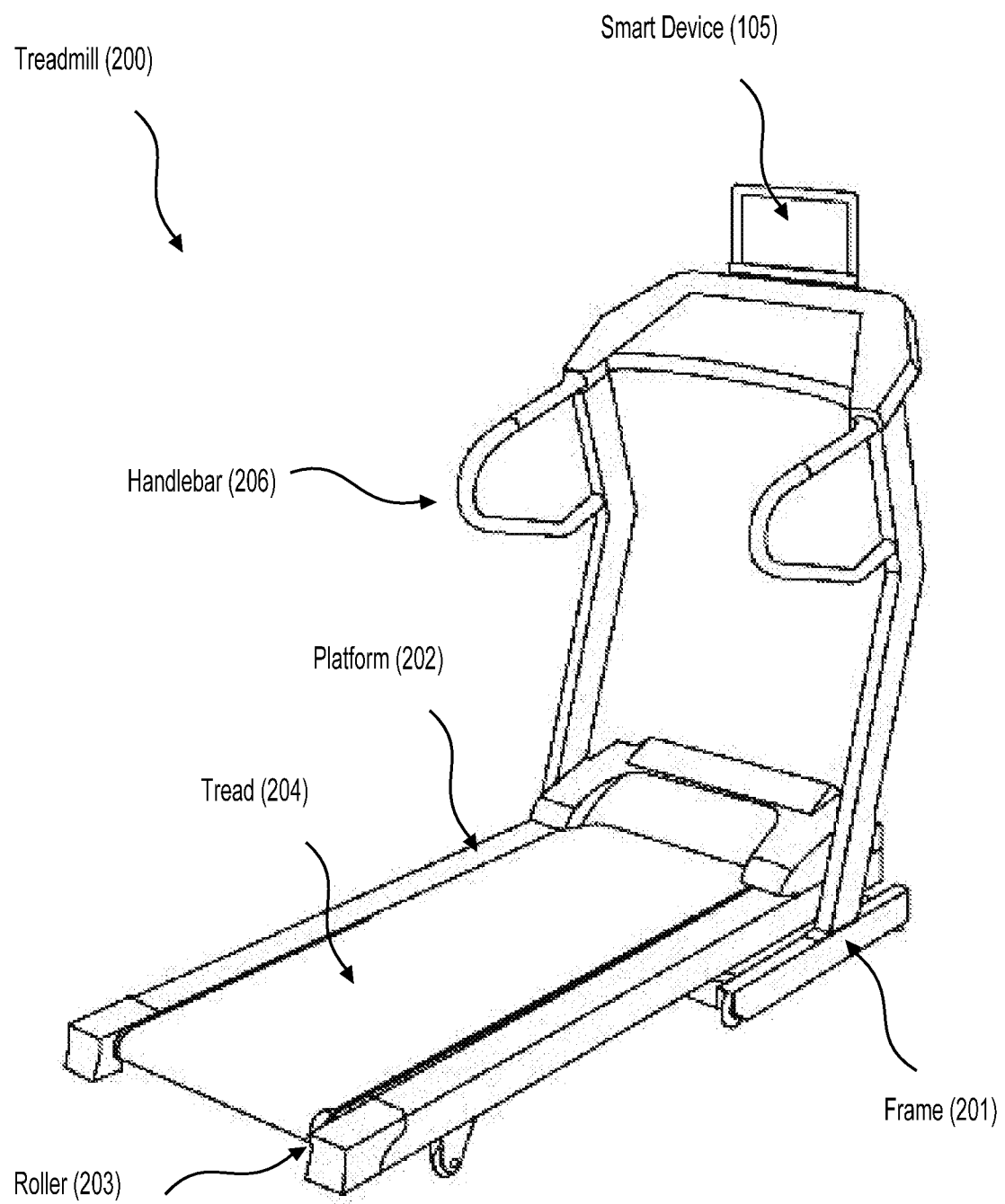
FIG. 2 shows a treadmill according to an example embodiment.

In an example embodiment, the exercise machine can be a treadmill. FIG. 2 shows a treadmill 200 according to an example embodiment. The treadmill 200 can include a frame 201, a platform 202, a roller 203, a tread 204, a smart device 105 and a handlebar 206. Similar to the exercise bike of FIG. 1, the treadmill 200 can include a generator which is mechanically connected or coupled to the roller 203 or the tread 204. When a user runs on the treadmill 200, the tread 204 rotates around the platform 202 and can cause the roller 203 to rotate. The rotation of the roller 203 can be mechanically transferred to the generator and the generator can generate electricity using this rotational movement. The smart device 105 can be paired with the generator such that the application of the smart device 105 can increase or decrease a load or resistance the generator imposes on the roller 203 and tread 204. Because the roller 203 is mechanically connected to the generator, an increase in the load or resistance of the generator can increase the load or resistance that the user feels while running on the tread 204.

In an example embodiment, the fitness device or generator is configured to detect data relating to the user's workout and communicate the data to the smart device. For example, the exercise bike 100 can measure a distance pedaled by the user while exercising and a number of calories burned by the user. This information can be determined based on the rotation rate of the flywheel 104 or the generator 106. The exercise bike 100 or generator 106 can communicate this data to the smart device 105. This communication can be wired or wireless. As another example embodiment, the treadmill 200 can measure a distance run by the user while running on the treadmill 200 and the treadmill 200 can communicate this information to the smart device 105. This information can be determined based on a rotation rate of the roller 203. In some embodiments, the application of the smart device can also calculate various metrics relating to the user's workout based on data measurements or detections communicated by the exercise machine or the generator. For example, if the exercise bike 100 communicates the rotation rate of the flywheel 104, the application can determine a distance pedaled by the user.

In this disclosure, an exercise bike and a treadmill are described as examples of a exercise machine. However, one of ordinary skill in the art recognizes that an exercise machine is not limited to exercise bikes and treadmills. Any exercise equipment or fitness equipment, including those that have a moving component, can be used as an exercise machine as described herein. Examples can include stair steppers, rowing machines, cross country skiing machines, climbing machines, elliptical trainers, weight machines and exercise machine hand pumps.

Electric Generator

In an example embodiment, the exercise machine can be coupled or connected to an electricity generator which can convert the mechanical energy generated by the exercise machine into electric power.

The electric generator can be an induction generator, which can generate electricity if its rotor is rotating faster than a synchronous speed of the generator. An AC asynchronous motor usually can be used as a generator, without any internal modifications. In generator operation, a prime mover such as a moving component of an exercise machine (e.g., flywheel 104 or roller 203) drives the rotor of the generator above the synchronous speed so that there is negative slip. The stator flux still induces currents in the rotor, but since the opposing rotor flux is now cutting the stator coils, an active current is produced in stator coils and the motor now operates as a generator, sending power back to the electrical grid.

The electricity generator can be a liner electric generator, which can have a sliding magnet that moves back and forth through a solenoid (e.g., a spool of copper wire). An alternating current is induced in the loops of wire by Faraday's law of induction each time the magnet slides through.

The generator, as described herein, can be connected to an electric power distribution network and supply the network with electric power. This connection can be made, for example, through a power management system. The power management system can include an inverter or other equipment such as a processor. In some embodiments, the generator can include the inverter and the generator can directly connect to an electric power distribution network. The inverter can monitor the power quality of the distribution voltage where the generator is connected. The inverter can alter the AC sine wave from the generator to match the grid. The inverter conditions the electricity to reduce risks of node failures.

In an example embodiment, the generator and/or inverter can include a transceiver for communication with a smart device. The transceiver can receive various commands or data from the smart device. The transceiver can also transmit various commands or data to the smart device. For example, the transceiver can receive a command to increase the resistance or load of the generator. Sending a signal to the generator, the inverter "allows" the generator to increase the amount of electricity produced by reducing the resistance on the electrical circuit and thereby increasing the amperage that is injected by the generator into the electrical grid. The transceiver can also receive an identification number of the user or smart device, e.g., when the smart device is being paired with the generator. The transceiver is also configured to transmit various informational messages or signals to the smart device. For example, the transceiver can transmit a message to the smart device indicating the rotational speed of the generator, data relating to the electricity generated by the generator such as current rate of electricity generation, etc. the transceiver can also transmit an identification number of the generator to the smart device.

Power Storage Unit

In an example embodiment, the generator can be connected to a power storage unit or an off-grid system. The power storage unit can be a battery. The generator can deliver power to the battery and the battery can store the power. The battery or the storage unit can be electrically connected to a household and can supply power to the household. For example, the energy stored in the battery can be used to power lightbulbs, refrigerators and other small appliances.

In some embodiments, the generator can be connected to a power management system, which can decide where to supply the power generated by the generator. For example, the power management system can determine to supply the power to a battery, when the battery is low in charge. The power management system can also decide to supply the power to the household. In some embodiments, the power management system can also decide to supply the power back to a grid (if there is one nearby).

In the embodiments that the generator supplies the power to a battery, the user can still be compensated for the user's workout. For example, the application of the smart device can determine the amount of electricity generated by the user and compensate the user for the generated electricity.

Tracker

In an example embodiment, the smart device can be paired with a tracker which can be a fitness tracker, an activity tracker, a wearable device or a health monitoring device. The tracker can monitor a user's health and collect data relating to, e.g., the user's vital signs or workout routine. For example, a tracker can collect data on a user's body temperature, blood pressure, heart rate, or breathing rate. Another exemplary tracker can collect other types of data. For example, a tracker can detect, measure or monitor the number of calories burned, blood oxygenation, the time spent exercising, distance swam, number of hours slept, etc. The tracker can be a single device such as a watch or can be implemented in multiple devices, e.g., a watch and a chest-strap heart rate monitor.

In some embodiments, the tracker can be paired with a smart device. Once paired with the smart device, the tracker can communicate its detected data with an application of the smart device. The application can be configured to display the data in a user interface of the smart device. In some embodiments, the application can be configured to communicate the detected data to a server. The server can aggregate the data collected from all users of trackers and further analyze the data. The server can discover patterns in the aggregated data, and based on the patterns, make predictions about or suggestions to a specific user. For example, the tracker can collect data about a specific user's sleeping habits and transmit it to the application. The application can send this data to the server and the server can compare the data to those collected from other users. Based on this comparison, the server might suggest to the user that the user sleeps less than other users of the tracking device.

In another embodiment, the application can receive data relating to a user's dietary habits. The application can also receive data from the tracker relating to the user's workout. Using the dietary data and tracker data, the application can analyze the user's workout, e.g., detecting patterns of increased endurance or performance based on the different dietary inputs. This analysis can optimize the user's performance.

Figure 3:
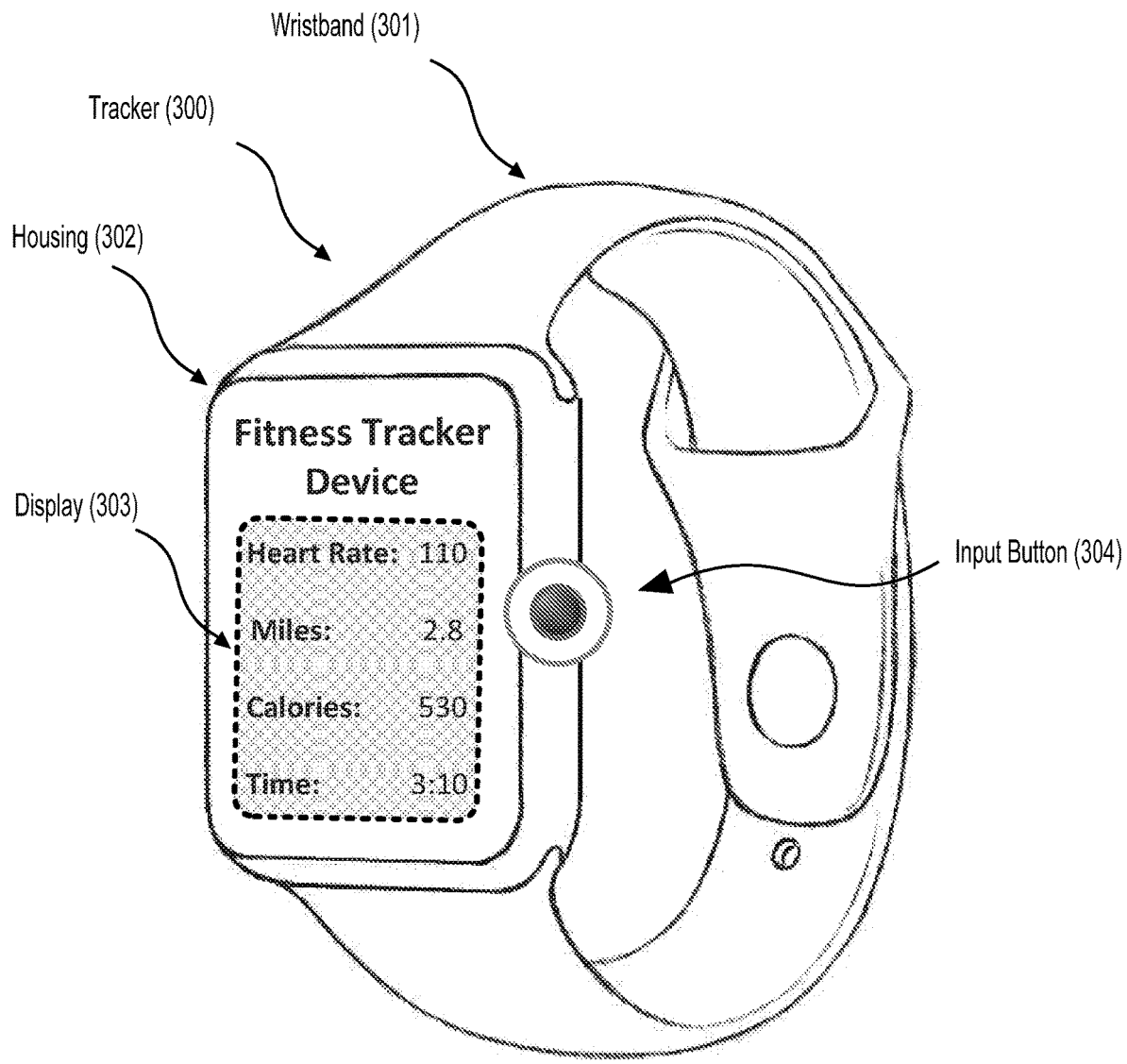
FIG. 3 shows a tracker according to an example embodiment.

FIG. 3 shows a tracker 300 according to an example embodiment. The tracker 300 can include a wristband 301, a housing 302, a display 303 and an input button 304. The display 303 can be an OLED, AMOLED, e-Ink, color paper ink, or other display screens known to persons of ordinary skill in the art. The display screen can be a touchscreen device, which can enable the tracker to receive touch commands from the user. A touch command can include performing one of the following actions on the screen of the tracker: tapping, double tapping, swiping, long pressing, long-press and dragging, double-tap dragging, pinching open, pinching closed, two fingers touching, two finger swiping, two finger long-pressing, two finger long-press swiping, two finger double tapping, and two fingers rotating.

The housing 302 can include processing circuitry such as a processor and a memory. The housing 302 can also include a sensor and a transceiver. Using the sensor, the tracker 300 can detect data relating to the user's vital signs or workout, e.g., heart rate or distance ran over the course of the workout. Using the transceiver, the tracker 300 can be paired and communicate with a smart device. The display 303 is configured to display some or all of the detected data to the user. For example, the display 303 can display the user's heart rate, distance ran and calories burned. The display 303 can also display other information to the user, e.g., time and temperature. The processing circuitry of the tracker 300 can command the transceiver to communicate the detected data to an application of a smart device.

In some embodiments, the tracker 300 is configured to be paired with a cellphone and the tracker 300 can function in connection with the cellphone. For example, the tracker 300 can receive phone calls and make phone calls through the cellphone. In these embodiments, the tracker 300 can include a microphone and a speaker. In other embodiments, the tracker 300 can display the user interface of the smart device which is paired with the tracker.

The input button 304 can be configured to provide input to the processing circuitry, e.g., the input button 304 can change the content displayed on the display 303 by selecting options displayed on the display 303. The input button 304 can also facilitate pairing of the tracker 300 with a smart device. For example, if the user holds the input button 304 for a predetermined period of time, the device can switch to discoverability mode (for pairing).

Application

In an example embodiment, a smart device is provided with an application which can be paired with a generator, an exercise machine and a tracker. The user can visit a service provider's website and download this application on the smart device of the user. The application can communicate with the generator, an exercise machine and a tracker, and send commands (or data) or receive data (or commands) from these devices. The application can include a user interface. The user interface of the application can display data received from the generator, exercise machine and tracker, e.g., the application can display data received from the tracker indicating how many calories the user has burned. The application can also command the generator, exercise machine and tracker, e.g., the application can command the generator to increase the load of the generator or exercise machine. The user interface of the application can display how much electricity has been generated by the user, and it can assign a monetary (or cyber-currency) value to the generated electricity. For example, the application can assign a cyber-currency denominated value to the generated electricity. This information can be determined based on the application's communication with the generator, a server of the service provider or a third-party device.

The user interface of the application can receive commands from a display of the smart device. The display of the smart device can be a touchscreen display device.

Account Sign-Up

In some embodiments, no account is needed for a user of the smart device to access the application. However, in an example embodiment, an application account is required for user of the smart device to access the application. The user can sign up for the application account using the application or the user can visit the service provider's website to sign up. The application or website can ask for the user's information such as the user's name, email address, username, password, etc. Upon receiving this information at a server of the service provider, the service provider can decide whether to open up the account for the user. This decision can be based on, e.g., whether the user's username exists in the system or whether the password meets the minimum requirements indicated on the service provider's website. In this embodiment, the user's information can be stored on the server of the service provider. However, in other embodiments, the user's information can be stored on the user's smart device. Once the sign-up process is complete, the user can log into the application.

Figure 4:
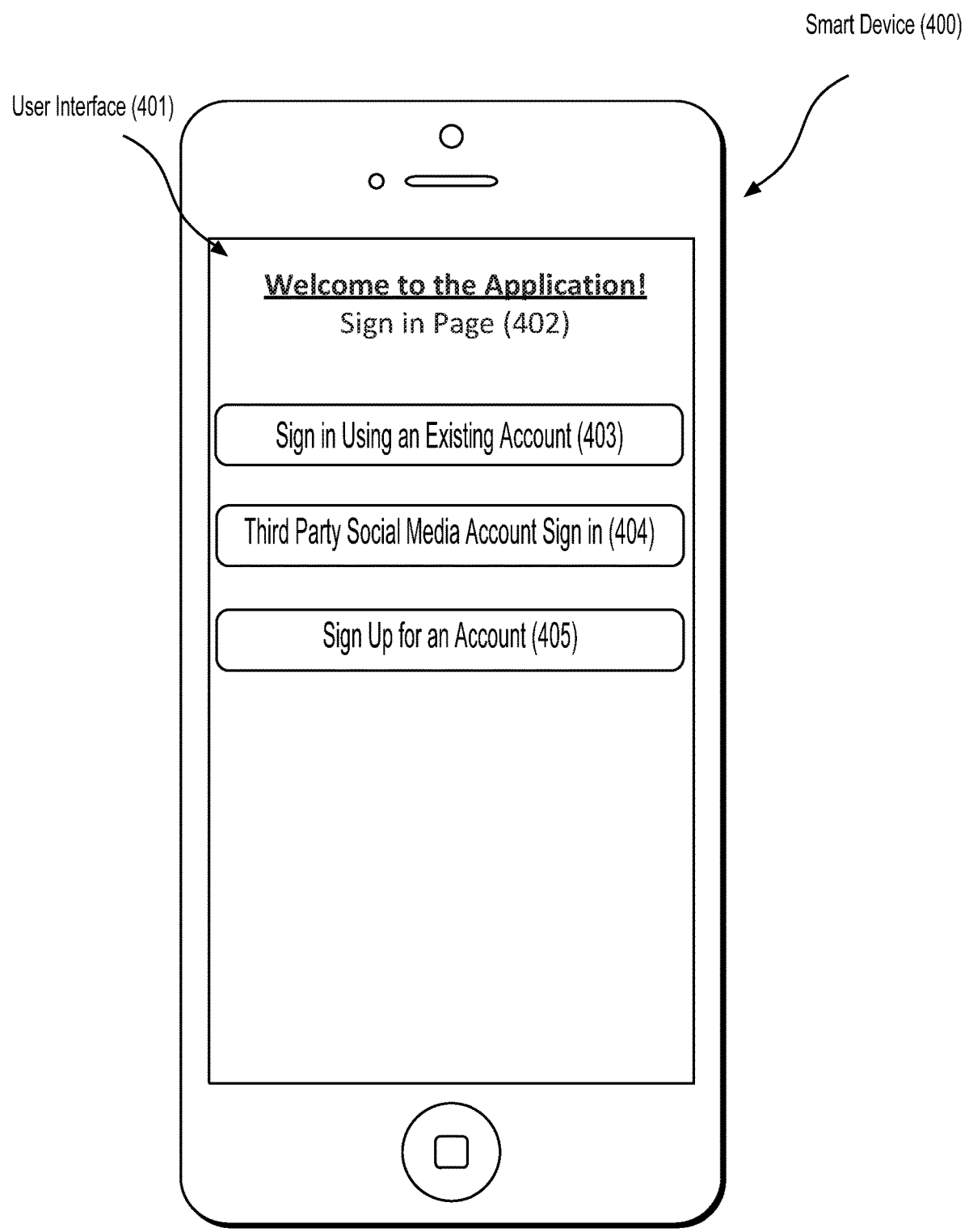
FIG. 4 shows a sign in page for a user interface of an exemplary application of a smart device.

FIG. 4 shows a sign in page for a user interface 401 of an exemplary application of a smart device 400. In this example embodiment, the smart device 400 includes an application which displays the user interface 401. The user interface 401 can display several pages, including a sign in page 402. On the sign in page 402, there can be several buttons, including a "sign in using an existing account" button 403, a "third party social media account sign in" button 404 and a "sign up for an account" button 405. Using the "sign in using an existing account" button 403, the user can sign into the application using the account that the user created with the service provider. Using the "sign up for an account" button 405, the user can sign up for an account, as described above. For example, by pressing this button, the user can be directed to a new page and the application can ask the user to enter information such as a username, password, etc.

Using the "third party social media account sign in" button 404, the user can sign into the application using a social media account belonging to a third party, e.g., a social media platform. For this option, the user's sign in credentials can be the same as the user's sign in credentials for the social media platform. In this case, the application can require the user to sign up for an account using the social media account before the application allows the user to access the application using the social media account credentials. The process of signing up for an account using the social media account can include redirecting the user to the social media platform, asking the user to sign into the user's social media account and selecting an option on the social media platform to indicate that the application is permitted to access the user's account or information.

User Profile

In an example embodiment, a user of the application can create a user profile, which can be associated with the application account. The user profile can be stored on the service provider's server or it can be stored on the smart device. The user profile can be created when the user signs up for the application account or after the user signs up. The user profile can include various information about the user. For example, a user profile can include a date of birth, an address, biometric information, information about the user's physique, a photo of the user, etc. In some embodiments, the user can upload information into the profile, e.g., machine generated information can be uploaded into the profile. For example, the user can upload fitness data gathered by a tracker into the user profile.

The information included in the user profile is not limited to information provided by the user. In an example embodiment, the service provider can also add information to the user profile. This information can be an interaction history of a user with the service provider, an analysis of the user's behavioral characteristics, a regression analysis and other analysis pertaining to the user's traits and habits. For example, a service provider can add information relating to a user's workout habit to a user's profile, e.g., how often the user exercises, frequently visited gyms, frequently used equipment, etc. As another example, the machine generated information about the user and the biographical information manually entered by the user can assist the server of the service provider in creating a health profile for the user. The health profile of the user can be stored in the user's profile. The health profile of the user can be used by the application, server of the service provider or social media platform to make predictions about the user or make suggestions to the user. For example, based on the user's health profile, the application, server of the service provider or social media platform can suggest the optimal number of weekly workouts per week that a user should complete. This determination can be based on the user's age group, physical fitness (e.g., weight, height and other information manually input into the application by the user), and other factors.

Figure 5:
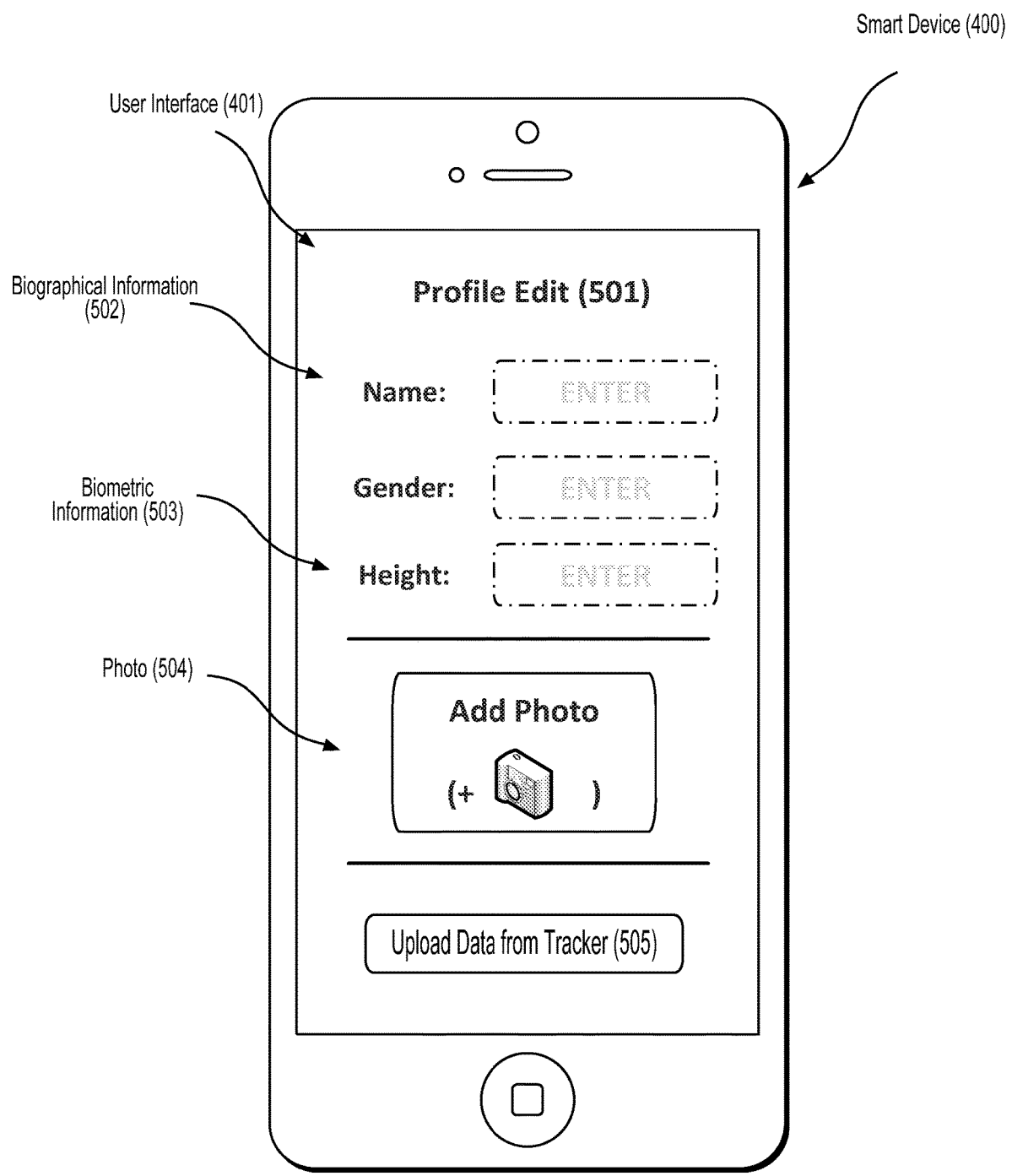
FIG. 5 shows a page for editing a user's profile on the application according to an example embodiment.

FIG. 5 shows a page 501 for editing a user's profile on the application according to an example embodiment. In the profile edit page 501, a user can enter the user's biographical information 502, e.g., name, hometown, alma mater, relationship status, biometric and soft-biometric information 503, e.g., height, weight, and gender. The user can also add a photo 504 to the profile. This photo, e.g., can be captured by a camera of the smart device, or it can be uploaded from the smart device or imported from the Internet, e.g., if social media is linked. The user can also upload data from a tracker by pressing the button 505. For example, the user can upload heart rate data from the tracker 300. Heart rate data can also be input manually into the application by the user and can include resting heart rate, maximum heart rate and heart rate zones. The application can use the information provided on the user's profile to make recommendations to the user or calculate required load on a generator.

Social Media Aspects of the Application

In an example embodiment, the user's application account or profile can be associated with a social media platform. The application can display and facilitate the user's interactions with the social media platform. For example, the application can display user profile pages, group profile pages, user posts and replies (or comments). As another example, the application can give the user the ability to draft a post and post it on the social media platform. As yet another example, the application can display the social media platform's news feed page. The social media platform can be a platform controlled by the service provider or it can be a platform controlled by a third party. In case the service provider controls the social media platform, the user can sign into the social media platform using the user's account credentials, e.g., the username and password associated with the application account. However, the user can have different credentials for the social media platform. For example, when the social media platform is operated by a third party, the user can sign into the social media platform using a username and password registered with the third party.

For each user, the social media platform can display a profile page which can include various information about the user. The social media platform can obtain this information from the user's application account or profile. In some embodiments, the user can provide the information to the social media platform independent of the user's application account or profile. The social media platform on the profile page can display the user's name, birthdate, location, photo, relationship status, etc. The user's profile page on the social media platform can also display the user's posts, replies to posts, activity log, favorite gym locations, groups joined, events attending and attended, friends, followers, following, electricity generated to date and similar statistics, workout statistics (e.g. total workouts, total time, averages, personal bests, etc.). The profile page can also show the amount and value of cyber-currency accumulated by the user.

Figure 6:
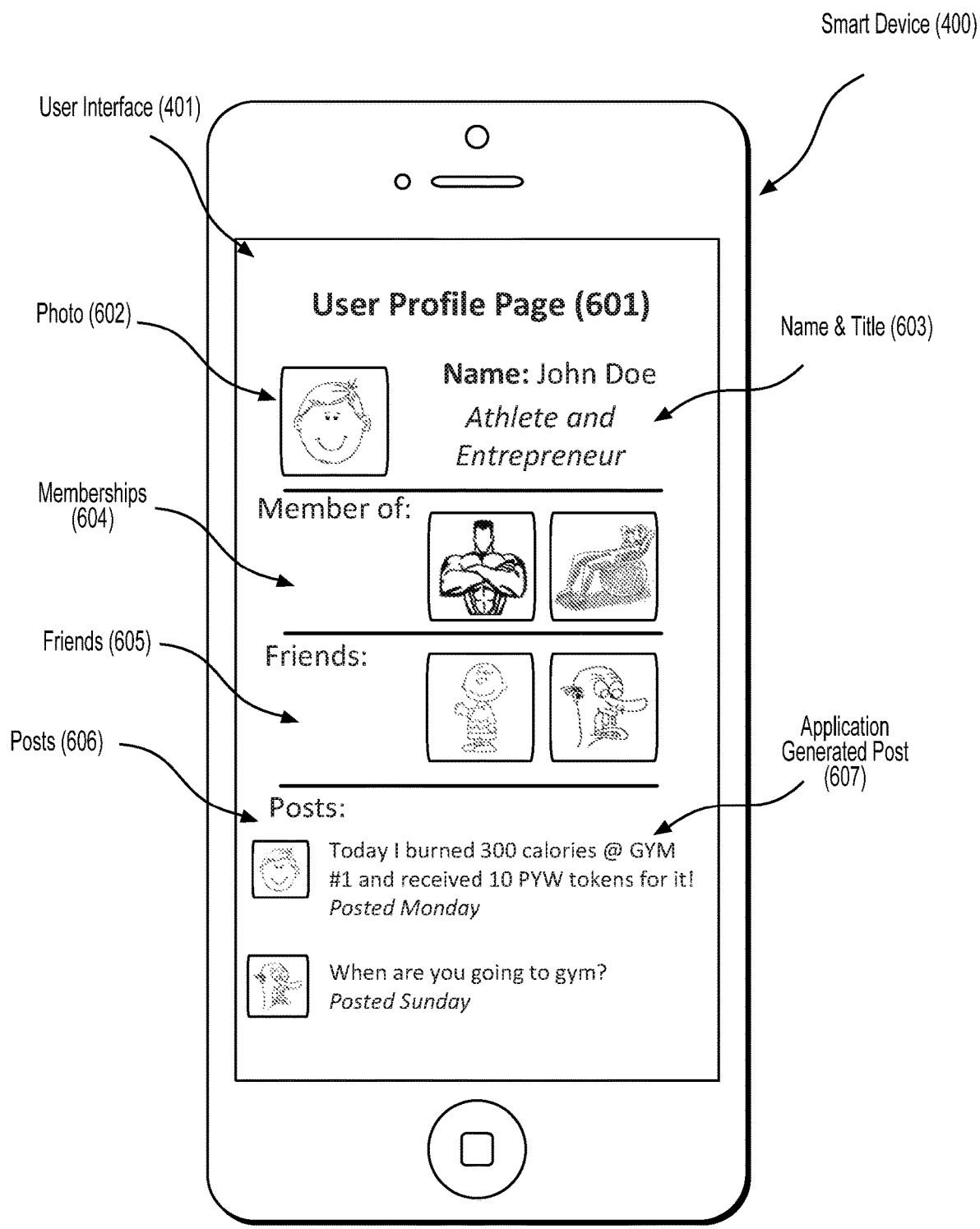
FIG. 6 shows an example user profile page displayed in the user interface of the application.

FIG. 6 shows an example user profile page 601 displayed in the user interface 401 of the application. In this example embodiment, the user profile page 601 can display the user's photo 602 and the user's name and title 603. This information can be obtained from the user's profile, which can be stored on the user's application or at a server of the service provider. The user profile page can also display the user's memberships 604 (i.e., the groups that the user has joined or is following) and friends 605. The user profile page 601 can also display the user's and other users' posts 606 on the user profile page 601.

The social media platform can be configured to establish links between various user profiles. For example, these links can be friendship links, follower links, alma mater links, location links, gender links, ethnic and other links (e.g., dating links), etc. These links can be established when a user of a profile requests the platform to establish a link between the user and another user or group of the social media platform. In an example embodiment, a first user can request a link with the profile of a second user. In some embodiments, the link can be established without any further action on the part of the second user, in which case, a follower link can be established between the first user and the second user such that the first user can follow the second user. In other words, the first user can follow the second user without the second user's confirmation, however the user will only be able to see the followed user's information that the followed user has made public or shared. In some embodiments, once the first user requests establishing a link with the second user, the second user has to approve the link request. For example, the second user has to confirm the first user as a friend before a friendship link can be established between the first user and second user. Once the second user approves the link request, the first user and the second user can become friends.

In an example embodiment, the social media platform can include various groups. A group can be an association between several user profiles who have joined the group. A group can also have a profile page, news and social feeds and privacy settings. Each group can include an administrator who can decide whether a user can join the group and what content can be displayed on the group's profile page. However, in some embodiments, joining a group does not require permission from the administrator. In these embodiments, the group members can decide the content displayed on the group's profile page. Sometimes the group members can also decide who joins the group. In an example embodiment, a user can join a group associated with a geographical location, a gym, and/or the fans of a particular workout.

In some embodiments, a user can follow a group. Depending on the group's privacy settings, following a group can provide fewer privileges to the user. For example, if a user joins a group after the administrator approves the user, the user can post content on the group's profile page. However, the administrator can set the privacy settings of the group such that only users who have joined the group can post on the group's profile page and the users who are following the group can only access the profile page.

In an example embodiment, a user can join a group associated with a gym. The gym director can be the administrator of the group. The administrator can communicate class schedules and hours of operation to the members of the group, e.g., by posting the schedules on the gym's profile page. In some embodiments, the administrator can also communicate to the members upcoming events at the gym, e.g., by directly messaging the group members. The group profile page can also provide the members with the ability to sign up for classes or upcoming events. For example, there can be a button next to each class or event on the group's profile page, and by pressing the button, the user can sign up for the class or event. The user can also mark a class as interested in attending or attending and post this information to their social media profile. The group profile page can also display the number of generators and exercise machine that are available at the gym for a given period of time. In some embodiments, the user can reserve a generator at the gym for a specific period of time. For example, if a user reserves a specific generator for a period of time, the generator can be locked to the user for that period of time so that no one else would be able to pair his or her smart device with the generator during that period of time. In these embodiments, the user can reserve the generator on the application or the social media profile page associated with the gym.

In some embodiments, a user can define various privacy settings for the user's profile page (or an administrator can define privacy settings for a group profile page). Using the privacy settings, the user can define whether the user's profile page is accessible to other users. More specifically, the privacy settings can define who can access the user's profile page and what can be displayed when the user's profile page is accessed by another user. In an example embodiment, the user can specify whether the user's friends, friends of friends, followers or other users can access the user's profile. For example, the user can specify that the user's profile page is accessible only to the user's friends. Therefore, the user's profile page is not accessible to any user who has not established a friendship link with the user. In another example embodiment, the user can specify which parts of the user's profile page can be visible to the users who have access to the user's profile page. For example, the user can specify whether all, some or none of the profile page of the user can be visible to another user.

In an example embodiment, a first user can visit the profile associated with a second user only if the second user's profile is accessible to the first user. Whether or not a second user's profile page is accessible to the first user depends on the privacy settings of the second user with respect to the first user. For example, a second user can designate the second user's profile page as public so that every visitor can access the content of the profile page. As another example, the second user can designate the user's profile page as semi-public. This indicates that depending on the status of the visitor, the visitor might not be able to access all of the content of the second user's profile page. As yet another example, the second user can designate the user's profile as private, in which case, only the visitors or groups of visitors who have been granted access privileges would be able to see the content of the second user's profile page.

In an example embodiment, the first user can draft a post and have the post displayed in a profile page on the social media platform. For example, the post can be a write-up discussing benefits of exercising. The post can include a photo, sound recording, a video, a media file, etc. The user can have the post displayed in the user's profile page or elsewhere, e.g., a page dedicated to an exercise group or even another user's profile page. A second user or the first user can draft a comment (or reply) in response to the first user's post and have the comment displayed in association with the first user's post. For example, the second user can draft a comment in response to the first user's write-up. The first or second user can also show their support for a post, comment or reply, and convey that they like it by clicking a button associated with each individual post, comment or reply. In some embodiments, the second user's ability to view and/or comment on the first user's post depends on the first user's privacy settings. For example, when drafting the post, the first user can specify which users can view the user's post, e.g., limiting the user's post to the user's friends or members of an exercise group.

In an example embodiment, the application of the user's smart device can post content onto the user's profile page or elsewhere. For example, the application can gather data relating to the user's workout and post this information on the profile page of the user. FIG. 6 shows an application generated post 607 on the user profile page 601. The application generated post 607 can include the number of calories the user burned out during the user's workout and the name of the gym at which the user worked. It can also include a monetary indicator representing how much the user was paid for the workout. For example, the application generated post 607 indicates that the user was paid by a cyber-currency named PYW (Power Your World) and that the user received 10 tokens of the PYW cryptocurrency.

In an example embodiment, the social media platform can include a news feed page, and the application is configured to display the news feed page. The news feed page can be an aggregation of social media posts and comments that have been posted by various users. For example, a news feed page can display the social media posts that have been generated over a period of time, e.g., 1 day, by the users or a subset of the users of the social media platform. The users or the subset of the users of the social media platform can be linked to the first user. In some embodiments, the news feed page is configured to display the posts of users who are not necessarily linked or related to the first user. For example, the news feed page can display posts and comments based on the user's profile information. Specifically, if the user's profile or health profile indicates a certain characteristic for the user, e.g., the user is interested in yoga and participates in yoga classes, the news feed page can display content related to this characteristic, e.g., posts from yoga instructors, or posts related to yoga groups.

In an example embodiment, the news feed page can display to the user posts by other users who are similar to the user in some respect, e.g., have similar profile information. The posts can include application generated posts displaying workout information for the other users. For example, for a user who is interested in running, the news feed page of the user can display workout data of other users who are interested in running. The data can include the number of calories burned, the name of the gym at which they worked out and the monetary value they received for their workout. Displaying workout data from users with similar profiles can encourage users to exercise more frequently.

Social Media Posts Relating to a User's Workout

In an example embodiment, the application can receive various data relating to a user's workout and post the data or a summary extrapolated from the data on the profile page of the user on the social media platform. The posting of the data can take place at the conclusion of a user's workout. For example, the user can participate in a spinning class. During the spinning class, the application of the user's smart device can adjust the resistance of the exercise bike based on a predetermined workout plan. The application can receive data relating to how much electricity was produced by the generator of the exercise bike, e.g., 12 kWh of electricity. The application can also receive data from a tracker indicating that the user has burned 1000 calories during the workout. Upon conclusion of the spinning class, the application can post this information on the user's profile page or on the gym's profile page. For example, the post can include the number of calories burned and the amount of electricity generated. The post can also indicate how much the user was paid for the electricity produced. This payment can be a value denominated by a cryptocurrency. Based on the privacy settings of the user, the post can be accessible to only a few users of the social media platform. However, in some embodiments, the post can be publically accessible. The post can also be shared with and posted to an unaffiliated third-party social media platform or application that the user uses if the user has registered, signed into, or linked the application to their unaffiliated, third-party social media accounts.

There are several techniques for the application of the smart device to determine that the user's workout has started or concluded. In a first exemplary embodiment, the application can include the class schedule for the gym. Therefore, using the class schedule, the application can determine when the workout has started and when the workout has concluded. In this embodiment, the user can sign up for the class using the application or the social media platform, and thus, the application receives data as to which classes the user intends to attend. For example, the user can indicate on the user's social media account that the user is attending a class and the social media platform can notify the application of the timing and location of the class. Hence, the application can determine when the class is started and when the class is over, and thus, determine when the user's workout has started and when it has concluded.

In a second exemplary embodiment, the application can determine the GPS coordinates of the user and based on these GPS coordinates the application can determine when the workout started and when the workout finished. For example, the application can determine that the workout has started when the user arrives at a location associated with a gym, and the application can determine that the user's workout has concluded when the user leaves the location. In some embodiments, the application can use the SSID of a Wi-Fi network for determining that the user is at a gym.

In a third exemplary embodiment, the application can determine that the user's workout has started or finished based on information received from devices paired with the application. For example, if the user connects a generator to the application and the user's tracker detects a higher than normal heart rate, the application can determine that the user's workout has started. As another example, if the user disconnects a generator from the application and the user's tracker detects a normal heart rate, the application can determine that the user's workout has concluded.

In a fourth exemplary embodiment, the application can determine that the user's workout has started or concluded based on information provided by the user. For example, the application can have a page on which the user can indicate that the user's workout has started or concluded. On this page, the user can also indicate whether the user intends to share the user's workout data. In a fifth exemplary embodiment, the application can determine that the user's workout has concluded based on a combination of the techniques discussed in the previous four exemplary embodiments. For example, the application can determine that the workout has concluded based on the user's GPS coordinates and based on a detection that the generator is disconnected from the application.

Paring the Smart Device and Other Devices

In an example embodiment, the user interface of the application can include a page for pairing the smart device with a generator, tracker or other device. Pairing the smart device with another device, e.g., generator, establishes an initial bonding between the smart device and the generator so that communication is allowed and facilitated between the two devices. In an example embodiment, the smart device can use Bluetooth wireless technology standard or Wi-Fi technology standard for exchanging data and communication between the smart device and the generator. Use of other wireless technology standards such as Induction Wireless, Infrared Wireless, Ultra Wideband, ZigBee, or a combination thereof are also conceivable.

In one embodiment, the smart device and the other device (e.g., generator or tracker) can be paired through a network such as the Internet. For example, the smart device can connect to the Internet through a cellular connection or via a router or hub. The generator can also connect to the Internet directly or through a router or hub. The generator can use Bluetooth or Wi-Fi wireless technology standard for exchanging data and communication between the generator and the router or hub. The hub can have a Wi-Fi connection to a router or a cellular connection to the Internet. The generator can also have a wired connection to the hub or router. In this embodiment, the smart device can exchange data and communicate with the generator using the Internet.

In an example embodiment, during pairing, a link key is used, which can be a shared secret known between the smart device and the generator (or tracker). If both devices store the same link key, they are said to be paired or bonded. In some embodiments, it is possible to limit the communication of the generator (or tracker) only to a smart device that was previously paired with the generator (or tracker). Such limitation can be implemented by cryptographical authentication of the identity of the smart device by the generator to ensure that the smart device is the smart device that was previously paired with the generator. Protection against eavesdropping is also possible by encrypting the exchanged data between the smart device and the generator. Users can delete link keys from either device, which removes the bond between the devices. It is possible for one device to have a stored link key for a device with which it is no longer paired.

Figure 7:
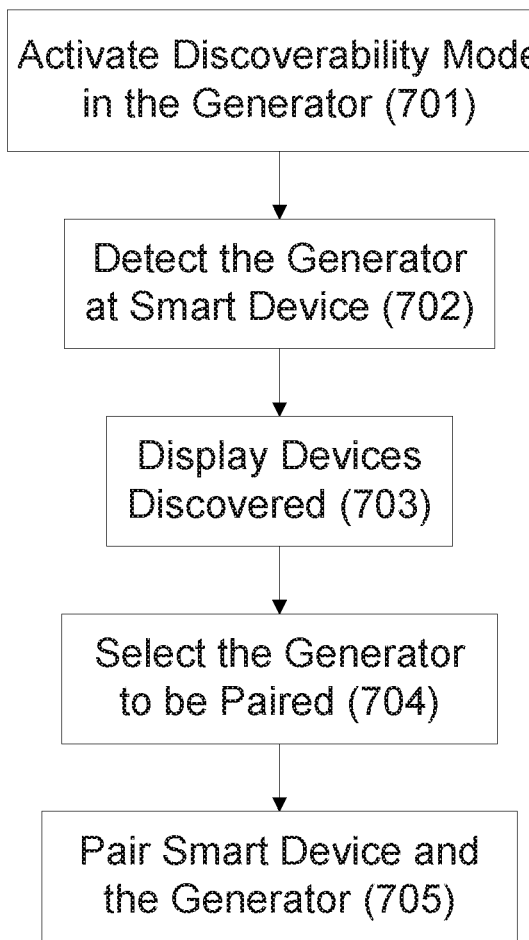
FIG. 7 shows an example flow process for pairing a smart device with a generator.

FIG. 7 shows an example flow process for pairing a smart device with a generator. In this example embodiment, pairing can start by a user initiation of a discoverability mode in the generator in step 701. In the discoverability mode, the smart device can detect the generator and let the user know the identity of the generator, for example, by displaying the identification number of the generator on the display of the smart device. The discoverability mode, for example, can be initiated by pressing the input button 304 in FIG. 3 for a few seconds. In step 702, the user can request the smart device to detect the devices around the smart device. For example, the user can make the detection request by choosing an "Add a Bluetooth Generator" or "Add a Wi-Fi Generator" on the smart device. Subsequently, the smart device seeks generators (and other devices) close to the smart device and at step 703, the smart device displays the identity of any generator (and other devices) discovered by the smart device. At step 704, the user can select the generator that the user intends to pair with the smart device. At step 705, the smart device can form a bond between the smart device and the generator, and the smart device and the generator will be able to communicate thereafter. Over the subsequent interactions, the smart device and the generator can connect to each other by reverting to the bond that has already been established. The user can sever the bond (i.e., deleting the link key) at any time, thereby terminating the communication link between the smart device and the generator. For example, the user can select a "Delete the Generator" option in the user interface of the smart device to sever the bond between the two devices. In some embodiments, an optional step can be provided after step 404. In this optional step, the user can be prompted to enter a password or login credentials on the generator to validate the pairing.

Figure 8:
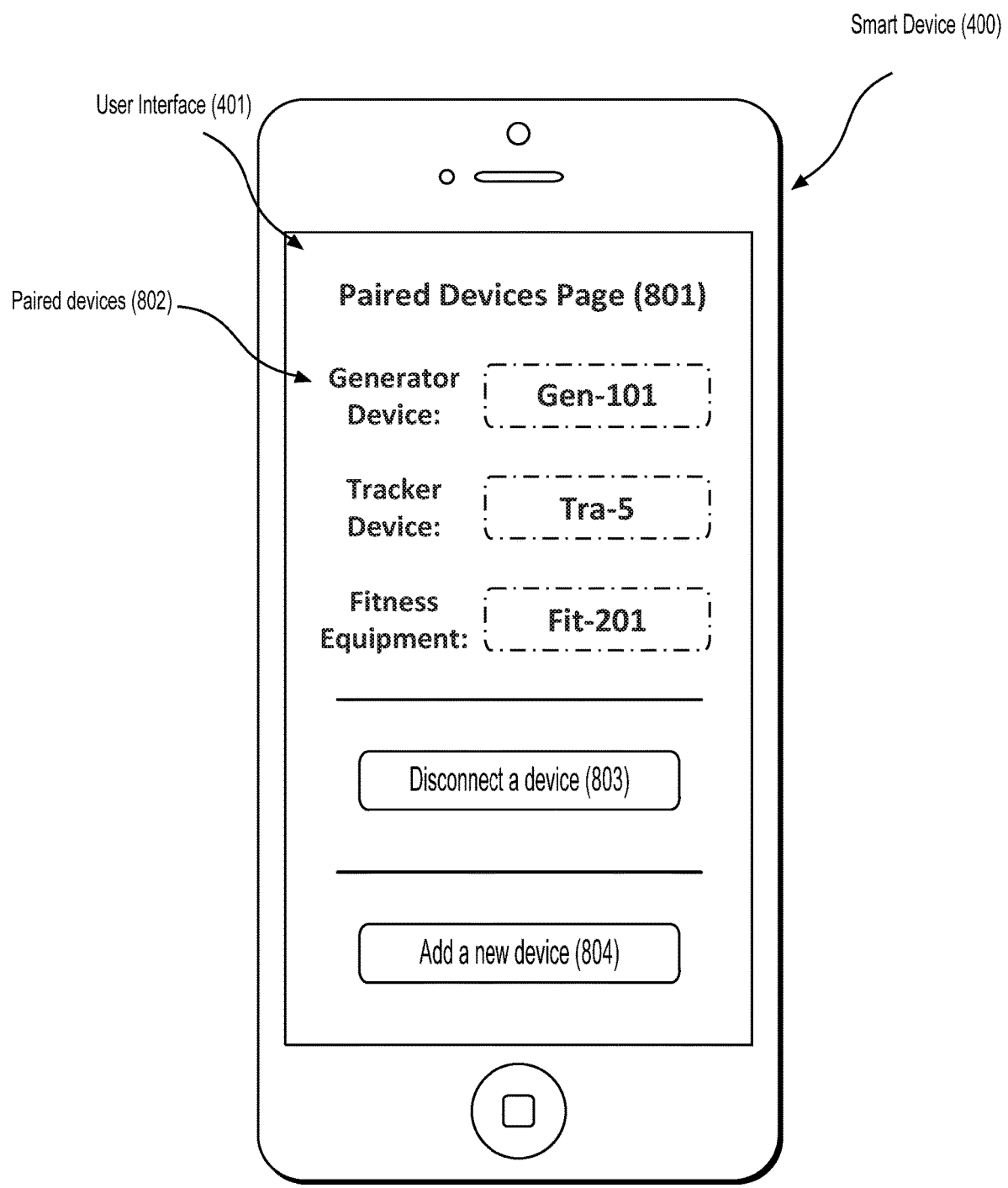
FIG. 8 shows a paired devices page in the user interface of the application according to an example embodiment.

In an example embodiment, the user interface of the application can include a page which displays all the generators, trackers and exercise machines currently or historically paired with the application of the smart device. FIG. 8 shows a paired devices page 801 in the user interface 401 of the application according to an example embodiment. In this example embodiment, the paired devices page 801 can display paired devices 802, which can include a generator Gen-101, a tracker Tra-5 and fitness equipment Fit-201. The paired devices page 801 can also include a disconnect a device button 803. Using this button, the user can disconnect any of the paired devices. The paired devices page 801 can also include an add a new device button 804. Using this button, the user can have the smart device 400 search for devices around the user so that the user can pair them with the smart device 400, as described above.

Resistance Adjustment

In an example embodiment, the user interface of the application can display a graphic icon for adjusting a resistance of an exercise machine or a generator. For example, the exercise machine can be an exercise bike, and the application can display a knob, a scroll bar or a field which can adjust the resistance of a generator paired with the smart device. In this example embodiment, the user can adjust the resistance by, e.g., rotating the knob, moving the thumb of the scroll bar or typing a number in the field on the user interface of the application. By taking any of these actions, or similar actions, the application can transmit a signal or message to the generator coupled to the exercise bike. In response to receiving this communication, the generator can increase its resistance or load. Because the generator is mechanically coupled to the exercise bike, the increase in the resistance of the generator can increase the load imposed on the flywheel of the exercise bike, and thus, the user can feel a heavier load when pressing the pedals of the exercise bike.

In some embodiments, the user interface can include an option for adjusting the resistance or other mechanical aspects of the exercise machine or generator according to a predetermined workout. For example, the user interface can include a page or a link to a page including several predetermined workouts. Once on the predetermined workout page, the user can select at least one of the workouts. The user can also create a customized workout for the user. Once the user selects a workout, the application determines a routine to be communicated to the generator. The routine can include generator loads to be imposed or exercise machine adjustments to be made during a period of time. For example, the application based on a predetermined workout routine determines that the workout includes a progressively increasing pedal load with the increases being implemented at 2-minute intervals (for a total of 10 minutes). As such, in one embodiment, at the end of every 2-minute interval, the application communicates a load increase message to the generator, and the generator implements the communicated load. In another embodiment, the application can communicate the entire workout routine to the generator, and the generator determines the load to impose (e.g., on a flywheel) during the workout based on the transmitted routine.

In an example embodiment, the application can adjust the resistance of the generator or the exercise machine to target a specific biometric reading, heart rate, blood pressure, blood oxygenation, etc. For example, a user can ask the application to target a heart rate of 160 bpm. Based on the user's profile (or health profile) which includes information about the user's physique (e.g., weight, gender, height, etc.), the application can determine that a heart rate of 160 bpm would require a specific load of the generator for a particular period of time. The application can transmit the load requirement to the generator.

Figure 9:
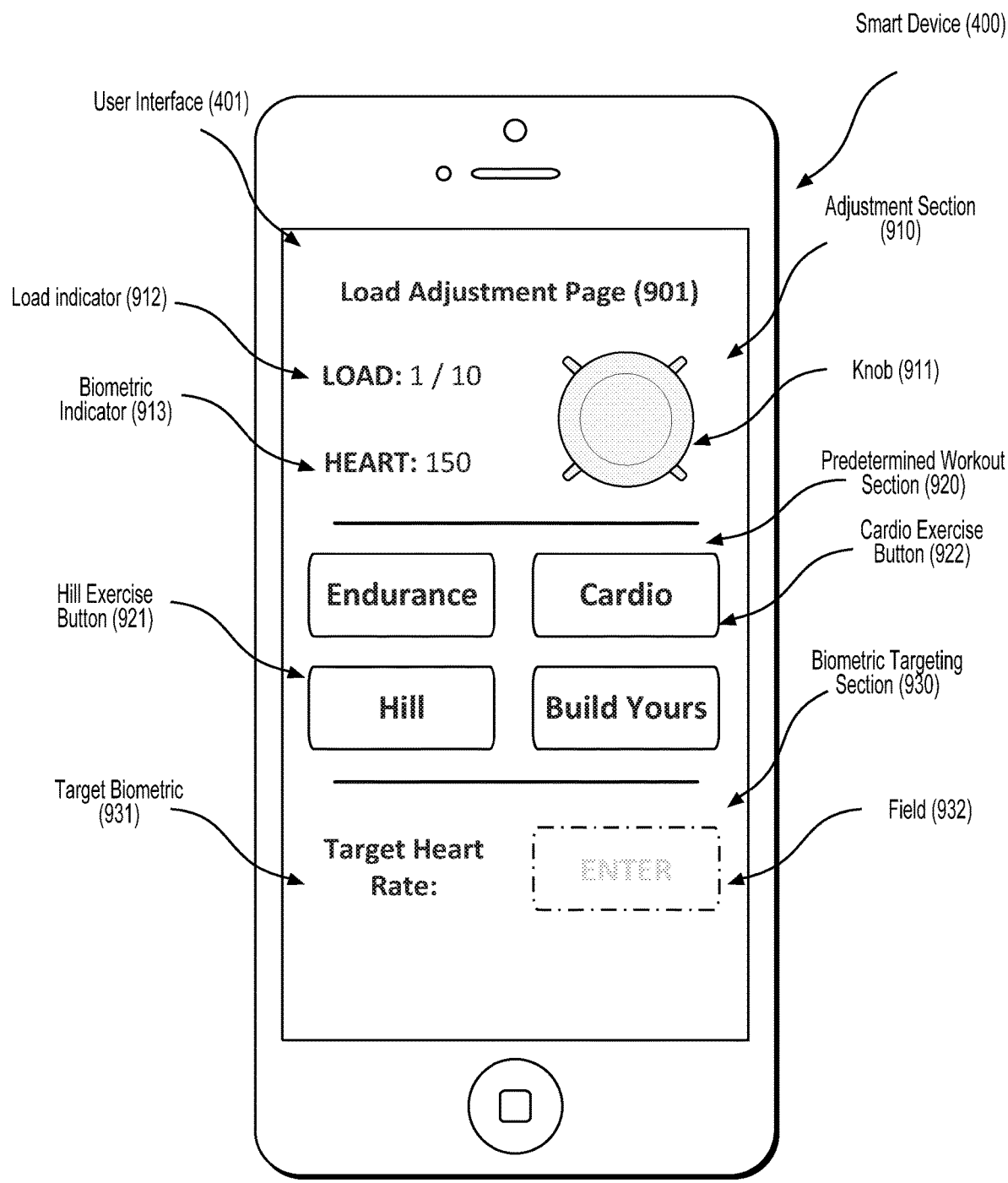
FIG. 9 shows a generator resistance adjustment page of the application according to an example embodiment.

FIG. 9 shows a load adjustment page 901 of the application according to an example embodiment. In this example embodiment, the user interface 401 can display the load adjustment page 901, which can include an adjustment section 910, a predetermined workout section 920 and a biometric targeting section 930.

The adjustment section 910 can include a knob 911, a load indicator 912 and a biometric indicator 913. By rotating the knob 911, the user can instruct the application to transmit a signal to the generator so that the load of the generator is adjusted. For example, the user can rotate the knob 911 clockwise to increase the load from 1 to 2. The load indicator 912 can display the current load of the generator. This load value can indicate the relative resistance that the user feels when exercising on the exercise machine. The application can determine the current load, e.g., by receiving a reading from the generator that indicates the load. As another example, the application can determine the current load by determining an initial load of the generator (e.g., zero) and any subsequent load adjustments that were communicated to the generator. In addition to knob 911, the user interface 401 can display other knobs. For example, the user interface can display a knob for an exercise machine paired with the application, e.g., the user interface 401 can display a knob for adjusting the slope of the platform 202 of the treadmill 200. The biometric indicator 913 can receive a signal from a tracker paired with the application and display the data included in the signal. For example, the biometric indicator 913 can display the instantaneous heart rate of the user detected by the tracker 300.

The predetermined workout section 920 can include several buttons for instructing the generator or exercise machine to emulate a specific workout routine, e.g., by adjusting the load of the generator or changing a setting of a component of the exercise machine for a particular time interval. As another example, the specific workout routine can include adjusting the load of the generator or changing a setting of a component of the exercise machine until a specific reading by a tracker is achieved. As yet another example, the specific workout routine can include adjusting the load of the generator or changing a setting of a component of the exercise machine to maintain a specific reading by the tracker for a time interval.

For example, the hill exercise button 921 can instruct the treadmill 200 to increase the slope of the platform 202 for 5 minutes and then decrease the load of the generator from 10 to 5 for 5 minutes. As another example, the cardio exercise button 922 can increase the load of the generator of the exercise bike 100 until the tracker 300 detects a heart rate of 150 bpm for the user. The application is configured to maintain this load of the generator for 10 minutes.

The biometric targeting section 930 enables the user to enter a biometric reading that the user desires to achieve. Subsequently, the application can instruct the generator to increase or decrease the load until the specified biometric reading is achieved. This section can include a target biometric 931 and a field 932. For example, the target biometric 931 can be a target heart rate and in the field 932 the user can enter a heart rate that the user desires to achieve, e.g., 150 bpm.

There are several ways for the application to adjust the generator load to achieve the targeted biometric reading. In one embodiment, the application can make a prediction about the target load of the generator based on the biometric information in the user's profile (or health profile). For example, based on the user's age, gender, weight and height the application can determine that a load of 5/10 is needed to achieve a target heart rate of 150 bpm.

In another embodiment, the server of the service provider can estimate the load needed to achieve a certain biometric reading. Here, for every user, the application can transmit certain information stored in the user's profile, the user's biometric reading from a tracker and the implemented load of the generator to a server of the service provider. For example, the application can continuously transmit the heart rate of the user, the user's weight and the load on the generator to the server. The server of the service provider can aggregate this information for all the users, and based on the aggregated information, make a model which can predict the load needed for a specific user to achieve a desired biometric reading. For example, the application can transmit a user's age, weight, gender and a desired biometric reading to the server, and in response the server can transmit an estimated load of the generator which would achieve the desired biometric reading for the user.

In yet another embodiment, the application can slowly increase or decrease the load of the generator until the desired biometric reading is achieved. For example, the application can increase the load of the generator every 30 seconds and monitor the user's heart rate. Once the desired heart rate is achieved, the application can stop adjusting the load of the generator.

The above described embodiments for achieving a desired biometric reading for a user are only exemplary. One of ordinary skill in the art recognizes that these embodiments can be combined to create other techniques for achieving a desired biometric reading for the user.

Location Based Determinations

In an example embodiment, the application can determine a current location of the smart device, and based on the current location, the application can suggest various options to the user. For example, the application can have an option for finding a gym close to where the smart device is located. If this option is activated, the application can ask the smart device to determine the current location of the smart device. Once the current location of the smart device is determined (e.g., GPS coordinates of the smart device), the application can look up a list of gyms located close to the current location of the smart device (or located within a defined distance of the current location of the smart device).

In some embodiments, the smart device stores the names and locations of certain gyms and the list of gyms close to the user can be determined by searching the storage device of the smart device. In other embodiments, the locations of the gyms are stored in a database of a server and the server can transmit this information to the smart device (e.g., upon a request by the smart device). Then, the smart device can search for the gyms that are within a close distance of the current location of the smart device. Yet in some other example embodiments, the smart device can transmit the current location of the smart device to the server, and in response, the server can transmit the names and locations of several gyms close to the smart device. The smart device is configured to display the list of gyms on the user interface of the smart device.

In an example embodiment, the user can ask the smart device to display gyms which include a particular device or service. For example, the user can ask the application to limit the list to the gyms which include spinning classes or treadmills. In another example embodiment, the user can ask the application to display only the gyms which include electric generators. These electric generators can be compatible with the application, and the user can pair the user's smart device with some or all of the electric generators provided in these locations. Yet in another example embodiment, the user can ask the application to display a list of gyms that are located within a defined distance of the smart device's current location and include a particular device or service. For example, the user can ask the smart device to show a list of gyms that include generators and are located within 5 miles of the current location of the smart device.

In an example embodiment, the application can include a reserve a generator page or feature. On the reserve a generator page, the user can locate a gym by, e.g., entering a zip code, name of the location, etc. Once a gym is located, the application can display how many generators are available for a specified period of time. The application can also display each generator that can be booked for the specified period of time, e.g., a list of the available generators and their respective identification numbers and model numbers. The application can also display a floorplan of the gym and show where each generator is located. The application can also display an identification number for each generator on the floorplan. The user interface of the application can allow the user to select a specific generator, e.g., by tapping on the generator on the floorplan of the gym, or by pressing a button next to the generator on the list of available generators. Once a generator is selected, the application can contact the gym and reserve the generator for the specified period of time.

Figure 10:
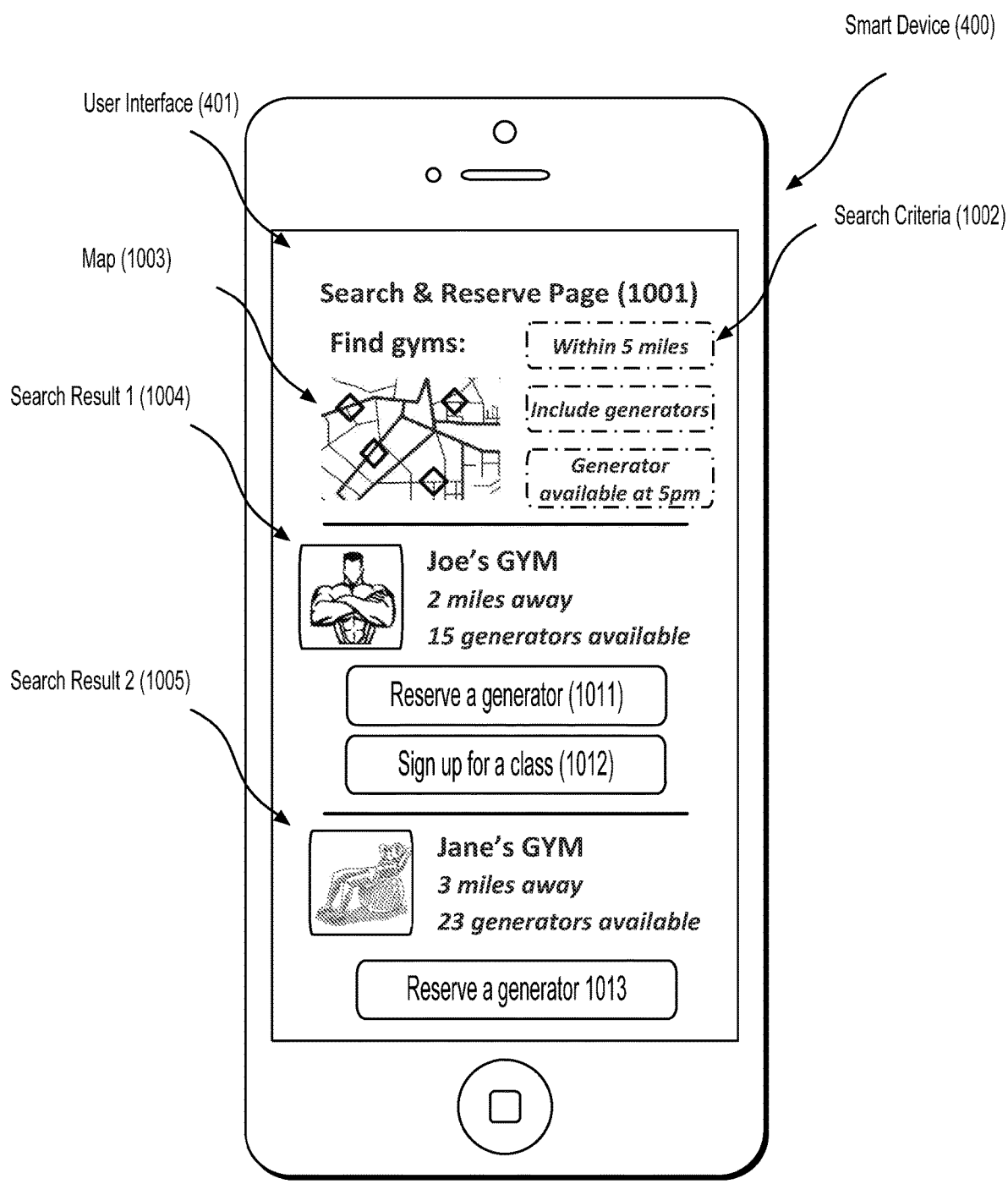
FIG. 10 shows an example search and reserve feature of the application according to an example embodiment.

FIG. 10 shows an example search and reserve feature of the application according to an example embodiment. In this embodiment, the user interface 401 of the application can display a search and reserve page 1001. In this example page, the user can specify at least one search criteria 1002 for finding a gym. For example, the user can specify that the user is looking for a gym within 5 miles of the current location of the smart device 400. The user can also limit the search results to gyms that include generators and that the generators are available at 5 pm. In response, the application can display the search results that fit the search criteria. For example, the application can display the search results 1004 and 1005. The application can display the names of these gyms, their respective distance to the current location of the smart device 400 and the number of generators each gym has available at the specified time. For example, Joe's gym has 15 generators available at 5 pm and Jane's gym has 23 generators available. The application can also display one or more buttons in association with each search result. For example, for the search result 1004, the application can display the button 1011 for reserving a generator at Joe's gym and the button 1012 for signing up for a class at the gym. The application can also display a map 1003 to show the search results on it. In some embodiments, the user can choose one of the search results by tapping on the map 1003.

Compensation and Cyber-Currency Features

In an example embodiment, a service provider can pay a user who produces electricity using a generator attached to an exercise machine. For example, a bank account of the user can be disclosed in the user's application account or profile. The service provider can deposit money into the bank account to pay the user for any electricity generated during a workout. In some embodiments, the service provider can issue a cyber-currency for payment to a user who produces electricity using a generator attached to an exercise machine. For example, an electronic wallet (or an address thereof) of the user can be disclosed in the user's application account or profile, and the service provider can pay the user at this electronic wallet. The cyber-currency can be a distributed peer-to-peer digital currency that can be transferred instantly and securely between any two users.

The cyber-currency can be regulated by cryptographic methods which manage and control the currency. For example, the cyber-currency can have a public key and a private key. The public key can be seen by others to verify the quantity of the currency at the specific address. The currency at the address can only be transferred to a third party by disclosing the private key. The private key can be a secret number that allows the cryptocurrency to be spent. Every cyber-currency address has a matching private key, which can be saved in the wallet file of the user who owns the balance. The private key can be mathematically related to the cryptocurrency address, and is designed so that the cryptocurrency address can be calculated from the private key. However, the same cannot be done in reverse. Private keys must be kept securely, for they authorize the release of cyber currencies at a specific address. Private keys can be kept on computer files (i.e., digital wallet), but they are also short enough that they can be printed on paper.

Private keys can also be kept on a virtual wallet, which can store a user's cyber currencies on a secure server where the cryptocurrencies can be accessed. Virtual wallets facilitate cyber-currency transactions. Virtual wallets also reduce the amount of risk in storing the cyber-currency because most virtual wallets store all or part of the user's cyber-currency balance on a server and the user's account is password protected or protected with two factor authentication.

In one embodiment, the supply of the cyber-currency tokens can be fixed after the service provider issues the cyber-currency tokens. For example, the service provider can issue and release all of the cyber-currency tokens at the same time. In another embodiment, the supply of the cyber-currency tokens can increase over time, but the ultimate number of the cyber-currency tokens in circulation can be fixed. For example, the service provider can issue new cyber-currency tokens until the supply of the tokens has reached its upper limit. In yet another embodiment, the supply of cyber-currency tokens can increase overtime without ever reaching a limiting number. This increase in the supply of the tokens can occur at an increasing rate or a decreasing rate.

There can be various techniques for paying a user for human generated electricity. In an example embodiment, the user is paid a fixed unit of a cryptocurrency for every kWh of electricity produced by the user. For example, the user can be paid 1.00 token of a service provider issued cryptocurrency for every kWh of electricity produced by the user. The cyber-currency can be exchanged in the market for other goods and services, and the market supply and demand can determine the relative value of the cyber-currency.

In another example embodiment, a service provider can set a rate for every kWh of electricity produced by the user. The service provider can determine this rate based on various factors including the supply and demand for human generated electricity, and thus, the rate can fluctuate over time. For example, a service provider can decide to compensate a user 0.75 token of a cryptocurrency for every kWh of electricity produced by the user. However, if the demand for human generated electricity increases in the market, the service provider can pay 1.00 token of the cryptocurrency for every kWh of electricity. This increase in price can encourage the users to produce more electricity and meets the market demand.

Various companies can request human generated electricity, e.g., to promote a healthy society. In an example embodiment, the service provider can issue certificates for each kWh of human generated electricity and the service provider can sell the certificates to these companies. These companies can purchase the certificates to bolster their mission of promoting a healthy society. For example, the service provider can require the companies to pay for the certificates using the service provider issued cryptocurrency. By requiring the companies to pay for the certificates using the cryptocurrency, the service provider can create a market for the cryptocurrency. In this market, the producers of human generated electricity (i.e., the users of the application) receive and supply the cryptocurrency and the companies demand the cyber-currency. Therefore, the market can determine a price for the tokens of the cyber-currency. As another example, the service provider can require a payment for the certificates in US Dollars. Because gyms that implement the generators save in their electricity bill, the service provider can also require the gyms to share part of the savings with the service provider.

There are several techniques for the service provider to determine how much electricity a user has produced. In one embodiment, based on the signals that the application receives from the generator, e.g., rotation rate or resistance, the application can determine how much electricity has been produced during the workout of the user. The application can communicate a message to the service provider indicating the amount of electricity that has been produced by the user. Based on this amount, the service provider can determine a payment to the user. The service provider can also initiate the payment, and the application can display the payment in the user interface, e.g., transaction history 1104.

In a second embodiment, the generator can be in communication with a server of the service provider. This connection can be a direct connection, e.g., Wi-Fi connection through the Internet, or it can be an indirect connection, e.g., the generator can be in contact with a power management system which communicates with the server. The generator or the power management system can transmit a signal to the server indicating the amount of electricity that was produced during the user's workout. Subsequently, the server can determine the user's reward for the workout, and the service provider can initiate a payment to the user. In this embodiment, the application can optionally transmit the generator's identification number to the server so that the server can determine which user is using the generator. It is also possible that the generator can transmit the user's identification number to the service provider. The generator can receive the user's identification number at the time of pairing.

In a third embodiment, the application can determine the user's payment. In this embodiment, the service provider can transmit a price to the application of the user. Based on electricity generation information received from the generator and the price, the application can determine how much money is owed to the user. The application can transmit a request to the server of the service provider and the service provider can initiate a payment to the user.

Several techniques for rewarding a user for electricity production were described. One of ordinary skill in the art recognizes that these techniques can be combined to create other techniques.

Figure 11:
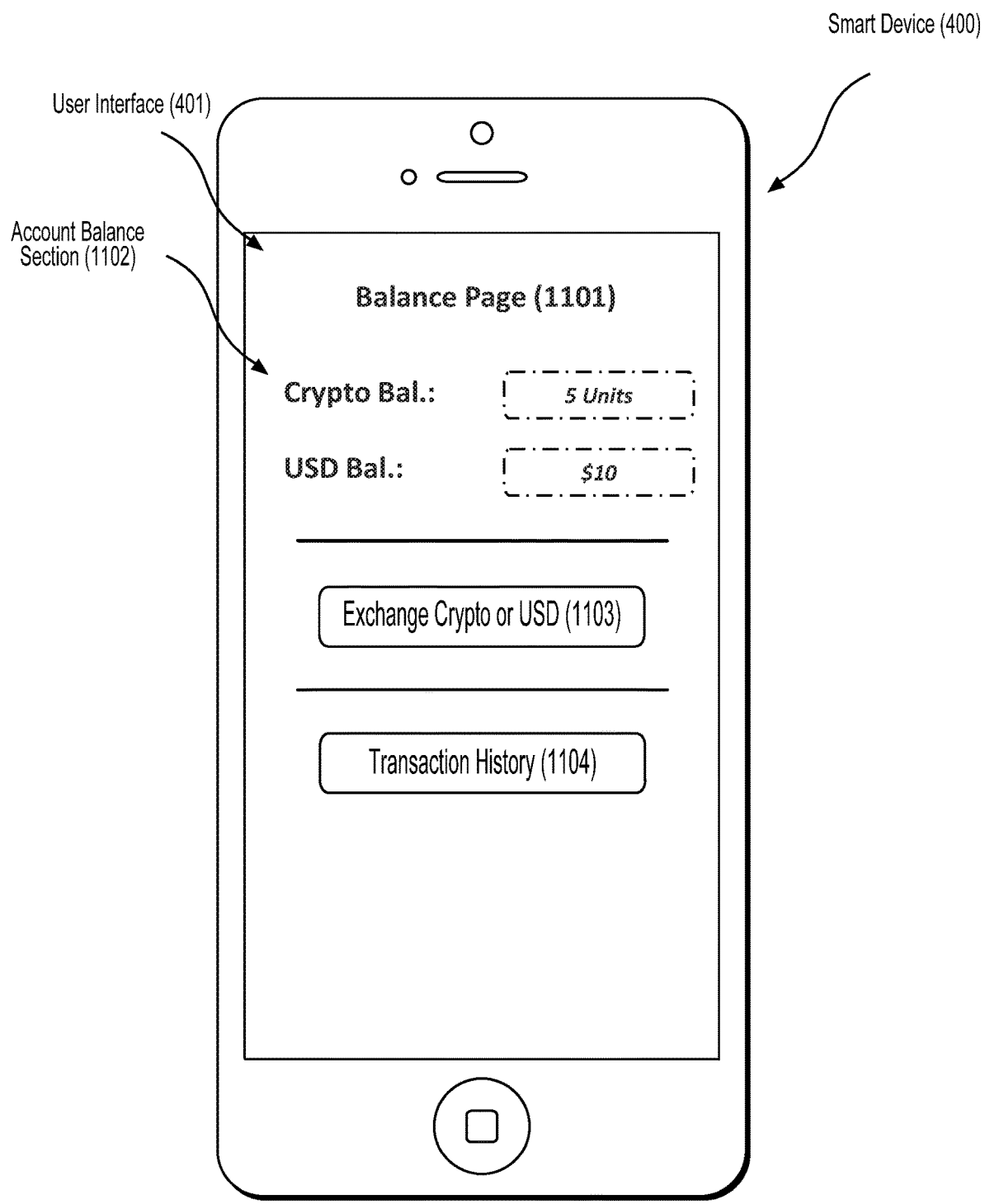
FIG. 11 shows a balance page displayed on the user interface of the application according to an example embodiment.

FIG. 11 shows a balance page 1101 displayed on the user interface 401 of the application according to an example embodiment. The balance page 1101 can include an account balance section 1102, which can display a cyber-currency balance for the user. In this embodiment, the user has accumulated the balance as a result of the user's workout.

This balance can be stored in a virtual wallet or it can be stored on the user's smart device. The account balance section 1102 can also include a conventional currency balance e.g., US Dollar ("USD") balance. In some embodiments, the user can be paid in USDs for the user's electricity production. In other embodiments, this balance can be accumulated because the user has traded some of the user's cyber-currency tokens for USDs.

The balance page 1101 can include an exchange USD button 1103. This button can facilitate a cyber or conventional currency exchange. Using this button, the user can contact the service provider or other parties to exchange the user's balance in one account, e.g., the cyber-currency balance, with another currency, e.g., USD. For example, by pressing the button 1103, the application can receive a quote for the outstanding balance of the cyber-currency displayed in the balance page 1101. This quote can be received from the service provider or others. The application can display the quoted price to the user, and if the user agrees, the application can sell the user's cyber-currency tokens and receive payment for the sale.

The balance page 1101 can also include a transaction history button 1104. Using this button, the user can ask the application to display the user's transactions in the cyber-currency or USD. For example, the application can display all the payments that the user received to reward the user for the user's electricity production. The application can also display all the exchanges of the cryptocurrency with other currencies.

Figure 12:
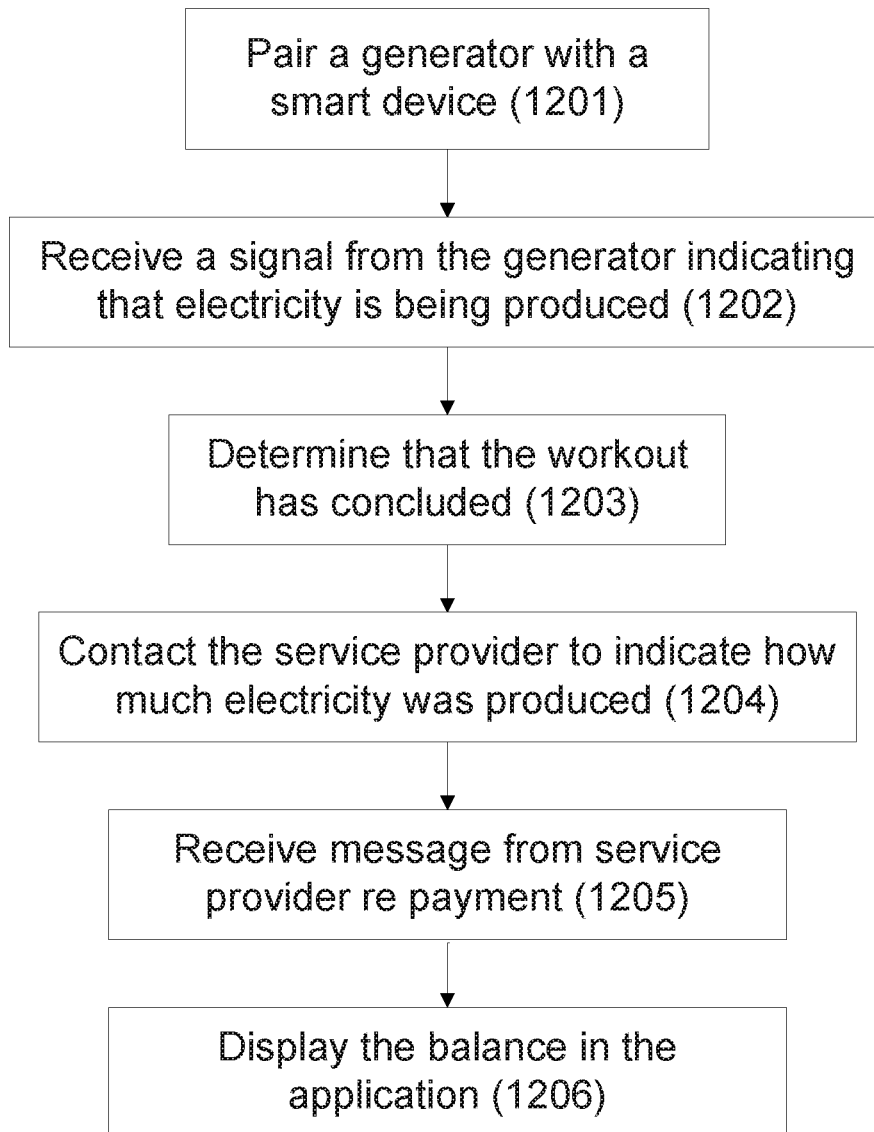
FIG. 12 illustrates a flow process for rewarding a user for human generated electricity according to an example embodiment.

FIG. 12 illustrates a flow process 1200 for rewarding a user for human generated electricity according to an example embodiment. In the step 1201, a user pairs a smart device with a generator connected to an exercise machine. Then, the user exercises on the exercise machine, and in step 1202, the generator transmits signals to the smart device indicating that the generator is producing electricity. For example, the generator transmits a rotation rate of the generator. Then, once the user finishes exercising, in step 1203, the smart device determines that the workout is concluded. In step 1204, the smart device contacts the service provider and informs the service provider how much electricity was generated by the user. Subsequently, the service provider determines how much to pay the user for the electricity production, and in step 1205, the service provider transmits a message to the application indicating a payment. In step 1206, the application displays a balance for the user's account indicating that the user received the payment for the workout.

In this disclosure, conventional money, cyber-currency and cryptocurrency are used as examples of valuable items that can compensate a user for the user's workout. However, disclosure is not limited to these examples. One of ordinary skill in the art recognizes that a user can be compensated using other tangible or intangible items of value. Moreover, one of ordinary skill in the art understands that for some aspects of this disclosure, cyber-currency and cryptocurrency (or even conventional currency) can be interchangeable.

Technical Implementation of the Sever

Figure 13:
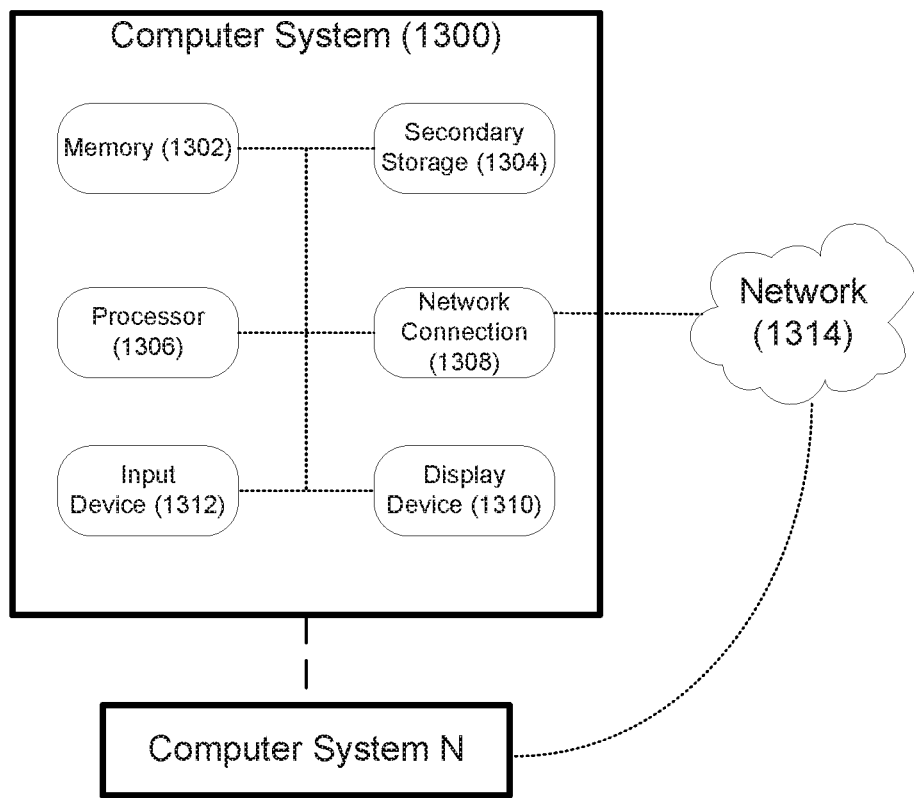
FIG. 13 illustrates exemplary hardware components of a server.

FIG. 13 illustrates exemplary hardware components a server of a service provider. A computer system 1300, or other computer systems similarly configured, may include and execute one or more subsystem components to perform functions described herein, including the steps of various flow processes described above. Likewise, a mobile device, a cell phone, a smartphone, a laptop, a desktop, a notebook, a tablet, a wearable device, a server, etc., which includes some of the same components of the computer system 1300, may run an application (or software) and perform the steps and functionalities described above. Computer system 1300 may connect to a network 1314, e.g., Internet, or other network, to receive inquires, obtain data, and transmit information and incentives as described above.

The computer system 1300 typically includes a memory 1302, a secondary storage device 1304, and a processor 1306. The computer system 1300 may also include a plurality of processors 1306 and be configured as a plurality of, e.g., bladed servers, or other known server configurations. The computer system 1300 may also include a network connection device 1308, a display device 1310, and an input device 1312.

The memory 1302 may include RAM or similar types of memory, and it may store one or more applications for execution by processor 1306. Secondary storage device 1304 may include a hard disk drive, floppy disk drive, CD-ROM drive, or other types of non-volatile data storage. Processor 1306 executes the application(s), such as those described herein, which are stored in memory 1302 or secondary storage 1304, or received from the Internet or other network 1314. The processing by processor 1306 may be implemented in software, such as software modules, for execution by computers or other machines. These applications preferably include instructions executable to perform the system and subsystem component functions and methods described above and illustrated in the FIGS. herein. The applications preferably provide graphical user interfaces (GUIs) through which users may view and interact with subsystem components.

The computer system 1300 may store one or more database structures in the secondary storage 1304, for example, for storing and maintaining the information necessary to perform the above-described functions. Alternatively, such information may be in storage devices separate from these components.

Also, as noted, processor 1306 may execute one or more software applications to provide the functions described in this specification, specifically to execute and perform the steps and functions in the process flows described above. Such processes may be implemented in software, such as software modules, for execution by computers or other machines. The GUIs may be formatted, for example, as web pages in HyperText Markup Language (HTML), Extensible Markup Language (XML) or in any other suitable form for presentation on a display device depending upon applications used by users to interact with the computer system 1300.

The input device 1312 may include any device for entering information into the computer system 1300, such as a touch-screen, keyboard, mouse, cursor-control device, microphone, digital camera, video recorder or camcorder. The input and output device 1312 may be used to enter information into GUIs during performance of the methods described above. The display device 1310 may include any type of device for presenting visual information such as, for example, a computer monitor or flat-screen display (or mobile device screen). The display device 1310 may display the GUIs and/or output from subsystem components (or software).

Examples of the computer system 1300 include dedicated server computers, such as bladed servers, personal computers, laptop computers, notebook computers, palm top computers, network computers, mobile devices, or any processor-controlled device capable of executing a web browser or other type of application for interacting with the system.

Although only one computer system 1300 is shown in detail, system 1300 may use multiple computer systems or servers as necessary or desired to support the users and may also use back-up or redundant servers to prevent network downtime in the event of a failure of a particular server. In addition, although computer system 1300 is depicted with various components, one skilled in the art will appreciate that the system can contain additional or different components. In addition, although aspects of an implementation consistent with the above are described as being stored in a memory, one skilled in the art will appreciate that these aspects can also be stored on or read from other types of computer program products or computer-readable media, such as secondary storage devices, including hard disks, floppy disks, or CD-ROM; or other forms of RAM or ROM. The computer-readable media may include instructions for controlling the computer system 1300, to perform a particular method, such as methods described above.

The present disclosure is not to be limited in terms of the particular embodiments described in this application, which are intended as illustrations of various aspects. Many modifications and variations can be made without departing from its spirit and scope, as may be apparent. Functionally equivalent methods and apparatuses within the scope of the disclosure, in addition to those enumerated herein, may be apparent from the foregoing representative descriptions. Such modifications and variations are intended to fall within the scope of the appended representative claims. The present disclosure is to be limited only by the terms of the appended representative claims, along with the full scope of equivalents to which such representative claims are entitled. It is also to be understood that the terminology used herein is for the purpose of describing particular embodiments only, and is not intended to be limiting.

The invention claimed is:

1. A non-transitory computer-accessible medium having stored thereon computer-executable instructions for controlling a generator, wherein, when a computing arrangement executes the instructions, the computing arrangement is configured to perform procedures comprising:
   receiving, at a transceiver of a client device, a biometric reading;
   receiving a first input indicating a target biometric reading;
   generating a first signal configured to set a load of the generator to conform the biometric reading to the target biometric reading;
   transmitting, through the transceiver, the first signal to the generator;
   receiving, at the transceiver, a second signal indicating an amount of power generated by the generator;
   receiving, at the transceiver, information from a server indicating a price fora cryptocurrency; and
   displaying, in a user interface of the client device, a value for the amount of power generated by the generator using the price for the cryptocurrency.

2. The computer-accessible medium of claim 1, wherein the biometric reading is received from a tracker.

3. The computer-accessible medium of claim 1, wherein the biometric reading is a body temperature, a blood pressure, a heart rate, a breathing rate or a blood oxygenation rate.

4. The computer-accessible medium of claim 1, wherein the first input is provided through a display of the client device.

5. The computer-accessible medium of claim 1, wherein the first input is provided by a server.

6. The computer-accessible medium of claim 1, wherein the first signal is generated based on a prediction using information stored on a profile.

7. The computer-accessible medium of claim 6, wherein the information include age, weight, gender, or height.

8. The computer-accessible medium of claim 1, wherein the first signal is generated by the computing arrangement when performing procedures comprising:
   transmitting, using the transceiver, information stored on a profile to a server;
   receiving a target load from the server; and
   generating the first signal based on the target load.

9. The computer-accessible medium of claim 1, wherein the second signal is a rotation rate for the generator.

10. The computer-accessible medium of claim 1, wherein the computing arrangement is further configured to perform procedures comprising:
    receiving, at the transceiver, an updated biometric reading;
    comparing the updated biometric reading and the target biometric reading; and
    transmitting, from the transceiver, a third signal configured to adjust the load of the generator.

11. The computer-accessible medium of claim 1, wherein the computing arrangement is further configured to perform procedures comprising:
    posting a social media post, on a social media platform, the social media post showing the value for the amount of power generated by the generator.

12. The computer-accessible medium of claim 11, wherein the computing arrangement is configured to post the social media post after a workout is concluded.

13. The computer-accessible medium of claim 12, wherein the workout is concluded when a GPS coordinate of the client device changes by more than a threshold value.

14. The computer-accessible medium of claim 12, wherein the workout is concluded when an updated biometric reading, received through the transceiver, is within a threshold range.

15. The computer-accessible medium of claim 1, wherein the computing arrangement is further configured to perform procedures comprising:
    displaying a total amount of cryptocurrency accumulated.

16. The computer-accessible medium of claim 1, wherein the computing arrangement is further configured to perform procedures comprising:
    receiving a second input indicating a change in the load of the generator; and
    transmitting, using the transceiver, a fourth signal to the generator, wherein:
    the fourth signal is generated based on the second input; and
    the fourth signal is configured to change the load of the generator according to a pattern.

17. The computer-accessible medium of claim 16, wherein the second input indicates a predetermined workout pattern and the pattern is generated based on the predetermined workout pattern.

18. The computer-accessible medium of claim 16, wherein the fourth signal is configured to change the load of the generator incrementally.

19. The computer-accessible medium of claim 1, wherein the generator is coupled to an exercise machine.

* * * * *